(12) United States Patent
Miles et al.

(10) Patent No.: US 9,907,608 B2
(45) Date of Patent: Mar. 6, 2018

(54) VALVE TREATMENT DEVICES, SYSTEMS, AND METHODS

(71) Applicant: MITRAGEN, INC., Bothell, WA (US)

(72) Inventors: Scott D. Miles, Sandy, UT (US); Vernon D. Dahl, Woodinville, WA (US)

(73) Assignee: MITRAGEN, INC., Bothell, WA (US)

( * ) Notice: Subject to any disclaimer, the term of this patent is extended or adjusted under 35 U.S.C. 154(b) by 466 days.

(21) Appl. No.: 14/475,540

(22) Filed: Sep. 2, 2014

(65) Prior Publication Data

US 2015/0066015 A1 Mar. 5, 2015

Related U.S. Application Data

(60) Provisional application No. 61/874,313, filed on Sep. 5, 2013, provisional application No. 61/895,478, filed on Oct. 25, 2013.

(51) Int. Cl.
*A61B 18/14* (2006.01)
*A61B 18/12* (2006.01)
(Continued)

(52) U.S. Cl.
CPC ...... *A61B 18/1492* (2013.01); *A61B 18/1206* (2013.01); *A61B 90/39* (2016.02);
(Continued)

(58) Field of Classification Search
CPC ............ A61B 18/1206; A61B 18/1492; A61B 2018/00369; A61B 2018/00654;
(Continued)

(56) References Cited

U.S. PATENT DOCUMENTS

| 5,431,649 A | 7/1995 | Mulier et al. |
| 5,545,193 A | 8/1996 | Fleischman et al. |

(Continued)

FOREIGN PATENT DOCUMENTS

| WO | WO 2008/074026 | 6/2008 | |
| WO | WO2011/021948 | * 2/2011 | ........... A61B 5/0488 |

OTHER PUBLICATIONS

Francesco Maisano et al., Mitral Transcatheter Technologies, Rambam Maimonides Medical Journal, vol. 4, No. 3, Jul. 25, 2013.
(Continued)

*Primary Examiner* — Jaymi Della
(74) *Attorney, Agent, or Firm* — David L. Scott

(57) ABSTRACT

Medical device systems, methods and devices are provided for treating a valve in a heart to minimize valve regurgitation. The medical device system includes an RF energy source, a handle, a treatment catheter, and a treatment device. The handle is operatively coupled to the RF energy source and coupled to the treatment catheter. The treatment device includes exposed electrode portions of one or more electrodes operatively coupled to the RF energy source and configured to contact tissue of a valve annulus. Further, one or more of the exposed electrode portions include a marker associated therewith. With this arrangement, a physician may view the one or more markers and selectively activate particular exposed electrode portions with RF energy to selectively treat a portion of the valve annulus.

7 Claims, 15 Drawing Sheets

(51) Int. Cl.
*A61B 18/00* (2006.01)
*A61B 90/00* (2016.01)

(52) U.S. Cl.
CPC .............. *A61B 2018/00369* (2013.01); *A61B 2018/00654* (2013.01); *A61B 2018/00714* (2013.01); *A61B 2018/00791* (2013.01); *A61B 2018/00797* (2013.01); *A61B 2018/00821* (2013.01); *A61B 2018/126* (2013.01); *A61B 2018/1253* (2013.01); *A61B 2018/143* (2013.01); *A61B 2018/1407* (2013.01); *A61B 2018/1425* (2013.01); *A61B 2018/1435* (2013.01); *A61B 2018/1475* (2013.01); *A61B 2090/3966* (2016.02)

(58) Field of Classification Search
CPC ........... A61B 2018/00714; A61B 2018/00791; A61B 2018/00797; A61B 2018/00821; A61B 2018/1253; A61B 2018/126; A61B 2018/1407; A61B 2018/1425; A61B 2018/143; A61B 2018/1435; A61B 2018/1475; A61B 2090/3966; A61B 90/39; A61B 2018/0016; A61B 2018/00214; A61B 2018/00267
See application file for complete search history.

(56) References Cited

U.S. PATENT DOCUMENTS

| | | |
|---|---|---|
| 5,636,634 A | 6/1997 | Kordis et al. |
| 5,823,955 A | 10/1998 | Kuck et al. |
| 5,855,576 A | 1/1999 | LeVeen et al. |
| 5,948,009 A | 9/1999 | Tu |
| 5,980,563 A | 11/1999 | Tu et al. |
| 6,002,955 A | 12/1999 | Willems et al. |
| 6,050,993 A | 4/2000 | Tu et al. |
| 6,056,744 A | 5/2000 | Edwards |
| 6,113,593 A | 9/2000 | Tu et al. |
| 6,165,206 A | 12/2000 | Tu |
| 6,228,109 B1 | 5/2001 | Tu et al. |
| 6,235,024 B1 | 5/2001 | Tu |
| 6,267,781 B1 | 7/2001 | Tu |
| 6,283,962 B1 | 9/2001 | Tu et al. |
| 6,306,133 B1 | 10/2001 | Tu et al. |
| 6,330,478 B1 | 12/2001 | Lee et al. |
| 6,346,105 B1 | 2/2002 | Tu et al. |
| 6,355,030 B1 | 3/2002 | Aldrich et al. |
| 6,356,790 B1 | 3/2002 | Maguire et al. |
| 6,485,489 B2 | 11/2002 | Teirstein et al. |
| 6,551,312 B2 | 4/2003 | Zhang et al. |
| 6,569,163 B2 | 5/2003 | Hata et al. |
| 6,575,971 B2 | 6/2003 | Hauck et al. |
| 6,671,533 B2 | 12/2003 | Chen et al. |
| 6,893,436 B2 | 5/2005 | Woodard et al. |
| 6,916,317 B2 | 7/2005 | Falwell et al. |
| 6,926,715 B1 | 8/2005 | Hauck et al. |
| 7,229,469 B1 | 6/2007 | Witzel et al. |
| 7,232,422 B2 | 6/2007 | Gibson et al. |
| 7,935,108 B2 | 5/2011 | Baxter et al. |
| 7,938,827 B2 | 5/2011 | Hauck et al. |
| 8,172,829 B2 | 5/2012 | Farnholtz |
| 8,187,266 B2 | 5/2012 | Dickens et al. |
| 8,226,637 B2 | 7/2012 | Satake |
| 8,231,613 B2 | 7/2012 | Baxter et al. |
| 8,328,798 B2 | 12/2012 | Witzel et al. |
| 2002/0026127 A1 | 2/2002 | Balbierz et al. |
| 2005/0033446 A1 | 2/2005 | Deem et al. |
| 2006/0009756 A1* | 1/2006 | Francischelli .......... A61M 5/14 606/32 |
| 2006/0089637 A1* | 4/2006 | Werneth ............. A61B 18/1492 606/41 |
| 2008/0082099 A1 | 4/2008 | Dickens et al. |
| 2011/0264086 A1* | 10/2011 | Ingle ................. A61B 18/1492 606/33 |

OTHER PUBLICATIONS

International Search Report dated Mar. 30, 2015 for International App. No. PCT/US2014/054157 (19 Pages).

* cited by examiner

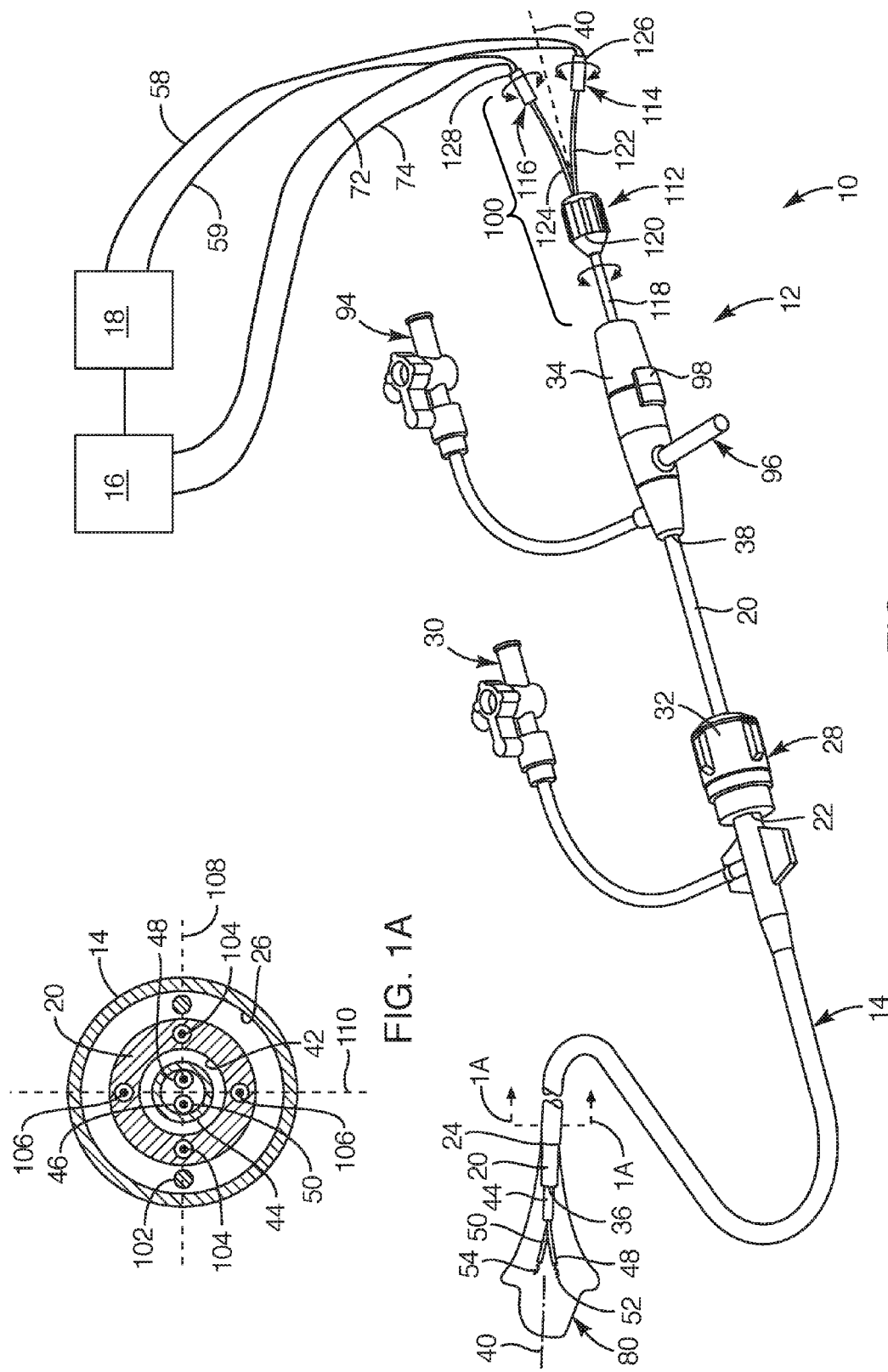

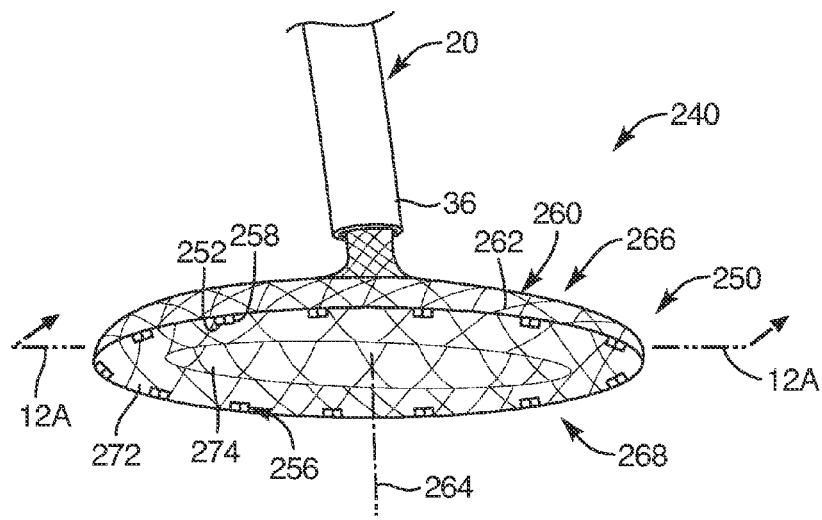
FIG. 12
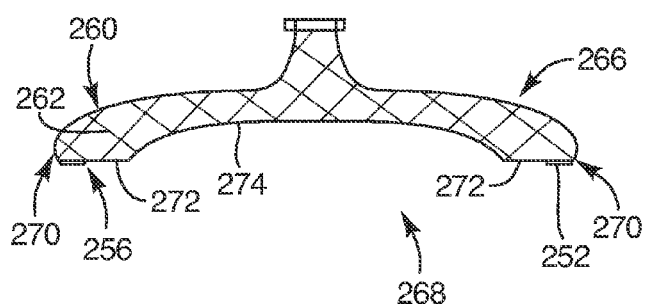
FIG. 12A
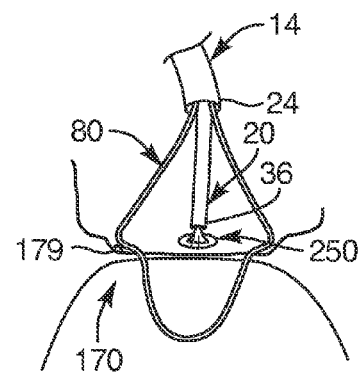
FIG. 13
FIG. 14

VALVE TREATMENT DEVICES, SYSTEMS, AND METHODS

CROSS-REFERENCE TO RELATED APPLICATIONS

The present application claims the benefit of U.S. Provisional Application No. 61/874,313, filed Sep. 5, 2013, and U.S. Provisional Application No. 61/895,478, filed on Oct. 25, 2013, the disclosures of which are hereby incorporated by reference in their entirety. This application relates to U.S. patent application Ser. No. 14/475,545, filed Sep. 2, 2014, titled VALVE TREATMENT DEVICES, SYSTEMS, AND METHODS, the disclosure of which is hereby incorporated by reference in its entirety.

TECHNICAL FIELD

The present invention relates generally to devices, systems, and methods for limiting valve regurgitation. More particularly, the present invention relates to medical devices, systems, and methods for percutaneously treating valves in, for example, the heart to limit valve regurgitation.

BACKGROUND

The human heart generally includes four valves: the mitral valve, the tricuspid valve, the aortic valve, and the pulmonic valve. Although all critical to heart function, the most critical one is the mitral valve. The mitral valve is located in an opening between the left atrium and the left ventricle. The mitral valve acts as a check valve and is intended to prevent regurgitation of the blood from the left ventricle in the left atrium when the left ventricle contracts. In preventing blood regurgitation the mitral valve must be able to withstand considerable back pressure as the left ventricle contracts.

The valve cusps or leaflets of the mitral valve are anchored to the muscular wall of the heart by delicate but strong fibrous cords so as to support the cusps during left ventricular contraction. In a healthy mitral valve, the geometry of the mitral valve ensures that the cusps overlie or touch each other to preclude regurgitation of the blood during left ventricular contraction. In contrast, the geometry is enlarged in an unhealthy mitral valve, which may prevent the leaflets from fully closing, resulting in mitral regurgitation.

Many known methods for treating mitral regurgitation resort to open heart surgery, typically by repairing the valve with a device or modifying the valve. Such procedures are expensive, extremely invasive requiring considerable recovery time and, most significantly, pose mortality risks. Further, such open heart procedures are particularly stressful on patients whom already have a cardiac condition. As such, open heart surgery is typically reserved as a last resort and is usually employed late in the mitral regurgitation progression. Moreover, the effectiveness of such procedures is difficult to assess during the procedure and may not be known until a much later time. Therefore the ability to make adjustments or modifications to the prostheses in order to obtain optimum effectiveness is extremely limited. Later corrections, if made at all, require still another open heart surgery bringing all of the risks and disadvantages discussed previously.

Other methods for treating mitral regurgitation have been proposed or implemented with some success, such as percutaneously implanting various clips in the chordae or at the valve cusps to assist in limiting valve regurgitation or prolapse. Although these methods have had some success and are non-invasive, the procedures are long and cumbersome, often taking several hours to complete. Further, due to leaving an implanted medical device in the heart, should the patient need additional subsequent procedures if, for example, regurgitation at the mitral valve again becomes an issue or the original regurgitation at the mitral valve is not corrected, another implanted device to correct the problem may be impossible at which time the patient's options may be limited to open heart surgery.

Based on the foregoing, it would be advantageous to employ a less invasive procedure to treat mitral regurgitation or any other types of valve regurgitation that overcome the disadvantages and issues resulting with the current invasive and non-invasive heart implants.

A variety of features and advantages will be apparent to those of ordinary skill in the art upon reading the description of various embodiments set forth below.

BRIEF SUMMARY OF THE INVENTION

Embodiments of the present invention are directed to various devices, systems and methods of a medical device system for treating a valve in a heart to minimize valve regurgitation. In one embodiment, the medical device system includes a radio frequency ("RF") energy source, a handle, a treatment catheter, and a treatment device. The handle is operatively coupled to the RF energy source and the treatment catheter is coupled to the handle. The treatment catheter extends between a proximal end and a distal end and includes a lumen defined along a length of the treatment catheter. The treatment device is disposed at the distal end of the treatment catheter and is moveable between a constricted position and an expanded position. The treatment device includes multiple strands extending in a woven configuration and, in the expanded position, is configured to be conformable to a valve annulus. The treatment device includes a lower periphery with exposed electrode portions of one or more electrodes, one or more of the exposed electrode portions including markers associated therewith. With this arrangement, the exposed electrode portions are configured to be selectively activated to heat a selective portion of the valve annulus.

In one embodiment, the medical device system includes a sheath defining a sheath lumen along a length of the sheath, the sheath lumen configured to provide a pathway to position the distal end of the treatment catheter adjacent the valve. In another embodiment, the medical device system includes an imaging member sized and configured to be positioned within the valve and is configured to provide imaging information regarding orientation of the valve. In another embodiment, the imaging member is configured to define the selective portion of the valve annulus to heat such that only the exposed electrode portions between portions of the imaging member are activated.

In another embodiment, the lower periphery of the treatment device is conformable to nest with at least a portion of the valve annulus. In another embodiment, a distal side of the treatment device includes a pad portion on which the exposed electrode portions are positioned. In another embodiment, the treatment catheter is configured to be steerable along a distal portion of the treatment catheter such that the distal portion is moveable to multiple orientations.

In another embodiment, the treatment device includes one or more temperature sensors. In another embodiment, the medical device system includes a controller coupled to the RF energy source and the one or more temperature sensors.

In accordance with another embodiment of the present invention, a medical device system for treating a valve in a heart to minimize valve regurgitation is provided. The medical device system includes an RF energy source, a handle operatively coupled to the RF energy source, a treatment catheter, and a treatment device. The treatment catheter is coupled to the handle, the treatment catheter extending between a proximal end and a distal end and including a lumen defined along a length of the treatment catheter. The treatment device includes a conformable elongate structure with a first elongate portion and a second elongate portion, the treatment device moveable between a first constricted state and a second exposed state. The first constricted state includes the first and second elongate portions extending alongside each other and the second exposed state includes the first and second elongate portions extending to a loop configuration, the loop configuration including exposed electrode portions of one or more electrodes. Further, one or more of the exposed electrode portions includes a marker associated therewith. With this arrangement, the exposed electrode portions are configured to be selectively activated to heat a selective portion of the valve annulus.

In one embodiment, the treatment device is moveable to the second exposed state with the first elongate portion maintaining a fixed linear position and the second elongate portion moved distally so that the treatment device exhibits the loop configuration. In another embodiment, the treatment device is moveable to the second exposed state by moving both the first and second elongate portions distally so that the treatment device exhibits the loop configuration.

In another embodiment, the treatment device includes one or more temperature sensors. In another embodiment, the medical device system includes a controller coupled to the RF energy source and the one or more temperature sensors.

In another embodiment, the medical devise system includes an imaging member sized and configured to be positioned within the valve and configured to provide imaging information regarding orientation of the valve. In still another embodiment, the imaging member is configured to define a selective portion of the valve annulus to heat such that only the exposed electrode portions between portions of the imaging member are activated.

In another embodiment, the treatment device includes one or more stabilizing members coupled to the treatment device and controlled from the handle. In another embodiment, the one or more stabilizing members facilitate pushing and pulling portions of the treatment device.

In accordance with another embodiment of the present invention, a medical device system for treating a valve in a heart to minimize valve regurgitation is provided. The medical device system includes an RF energy source, a handle operatively coupled to the RF energy source, a treatment catheter, and a treatment device. The treatment catheter is coupled to the handle, the treatment catheter extending between a proximal end and a distal end and including a lumen defined along a length of the treatment catheter. The treatment device is disposed at the distal end of the treatment catheter. The treatment device having an elongate arcuate portion with exposed electrode portions of one or more electrodes spaced along the elongate arcuate portion. The treatment device also includes one or more stabilizing members configured to push and pull portions of the treatment device to position the treatment device against a valve annulus.

In one embodiment, the medical device system includes an imaging member sized and configured to be positioned within the valve and configured to provide imaging information regarding orientation of the valve. In another embodiment, the imaging member is configured to define a selective portion of the valve annulus to heat such that only the exposed electrode portions between portions of the imaging member are activated.

In another embodiment, the treatment device includes one or more temperature sensors. In another embodiment, the medical device system includes a controller coupled to the RF energy source and the one or more temperature sensors.

In another embodiment, the elongate arcutae portion is configured to extend substantially planar. In another embodiment, the elongate arcuate portion is configured to exhibit an expandable and retractable loop configuration. In still another embodiment, the elongate arcuate portion exhibits a conformable ring configuration.

In accordance with another embodiment of the present invention, a method of treating a valve in a heart to minimize valve regurgitation is provided. The method includes the steps of: advancing a sheath adjacent to the valve; advancing a treatment catheter through the sheath to position adjacently above the valve; positioning a treatment device at a distal end of the treatment catheter over a valve annulus, the treatment device including exposed electrode portions of one or more electrodes positioned along at least a lower periphery of the treatment device so that the exposed electrode portions contact tissue of the valve annulus; viewing an imaging member positioned in the valve annulus and one or more markers associated with one or more of the exposed electrode portions; and selectively activating the exposed electrode portions of the one or more electrodes with an RF energy source operatively coupled to one or more electrodes such that only the exposed electrode portions of the one or more electrodes defined between portions of the imaging member are activated to selectively heat a portion of the valve annulus.

In one embodiment, the method includes the step of positioning the imaging member in the valve with the portions of the imaging member positioned over the valve annulus between a posterior portion and an anterior portion of the valve annulus. In another embodiment, the positioning step includes deploying the treatment device over the valve annulus such that the treatment device radially expands and conforms to at least the portion of the valve annulus. In another embodiment, the positioning step includes positioning the treatment device with stabilizing members coupled to the treatment device and controlled from a handle of the treatment device.

In another embodiment, the viewing step includes viewing the one or more markers relative to the imaging member. In another embodiment, the selectively activating step includes selectively activating the exposed electrode portions of the one or more electrodes to heat the tissue with an RF energy source operatively coupled to the one or more electrodes. In another embodiment, the selectively activating step includes selectively activating the exposed electrode portions operating in at least one of a bipolar mode and a unipolar mode.

In another embodiment, the method further includes the step of sensing a temperature of the tissue with one or more temperature sensors positioned on the treatment device. In another embodiment, the selectively activating step includes heating the tissue with the one or more electrodes to a temperature in the range of 50-85 degrees Celsius. In another embodiment, the heating step includes controlling the RF energy source from overheating the tissue with a controller coupled to one or more temperature sensors.

These various embodiments may include other components, features or acts as will be apparent from the detailed description set forth below. Additionally, other embodiments, configurations and processes are set forth below in the detailed description of the invention.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 1 is a perspective view of a medical device system, depicting an RF energy source and controller in schematic form, according to an embodiment of the present invention;

FIG. 1A is a cross-sectional view of the sheath and treatment catheter taken along section line 1A of FIG. 1, according to another embodiment of the present invention;

FIG. 12 is a perspective view of another embodiment of a medical device, depicting the medical device fully deployed from the treatment catheter and having a weave configuration, according to the present invention;

FIG. 12A is a cross-sectional view of the medical device taken along section line 12A of FIG. 12, according to another embodiment of the present invention;

FIG. 13 is a simplified view of the medical device partially deployed from the treatment catheter, depicting the medical device positioned over the imaging member, according to another embodiment of the present invention;

FIG. 14 is a simplified view of the medical device fully deployed over a mitral valve, depicting a periphery of the medical device having electrodes positioned over the posterior annulus and anterior annulus of a valve, according to another embodiment of the present invention;

DETAILED DESCRIPTION OF THE INVENTION

Figure 2A:
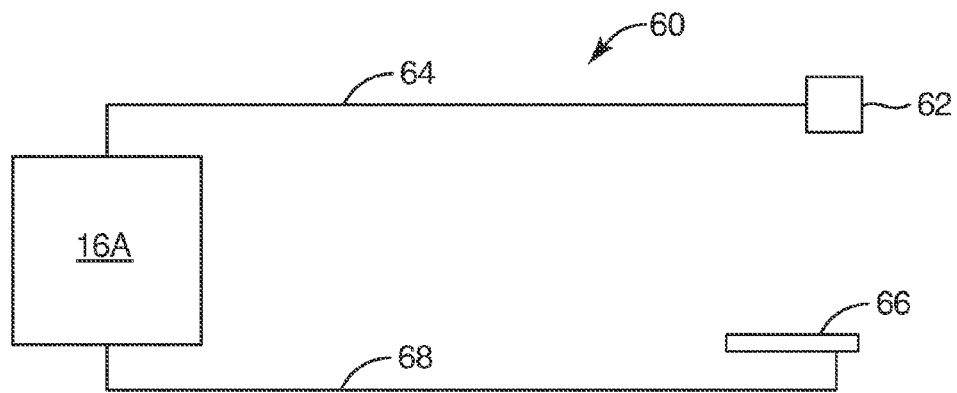
FIG. 2A is a schematic of the RF energy source and a unipolar electrode system, according to one embodiment of the present invention.

Referring first to FIG. 1, a medical device system 10 for treating valve regurgitation is provided. The medical device system 10 may include a treatment catheter system 12, a sheath 14, and a radio frequency ("RF") energy source 16. The RF energy source 16 may also be coupled to a controller 18 such that the controller 18 may be housed with the RF energy source 16. With such a medical device system 10, a distal portion of the sheath 14 may be advanced and positioned in the left atrium of the heart so that the treatment catheter system 12 may then be advanced through the sheath 14 to, for example, a valve in the heart, such as a mitral valve 170 (see FIG. 4). The treatment catheter system 12 may include one or more electrodes to be positioned to contact tissue of the valve, for example, the tissue of the posterior annulus of the valve. The one or more electrodes may be employed to heat the tissue of the valve to a predetermined temperature range with the RF energy source 16 at energy levels that may be modulated for a period of time. With this arrangement, the medical device system 10 may treat the valve by heating the tissue of the annulus, which results in the tissue shrinking, thereby, restoring the valve to normal size and function and to substantially reduce or prevent valve regurgitation.

Now referring to FIGS. 1 and 1A, as set forth, the medical device system 10 may include a sheath 14. The sheath 14 may be sized and configured to receive a treatment catheter 20 of the treatment catheter system 12 and, as such, the sheath 14 may be somewhat shorter in length than the treatment catheter 20. The sheath 14 may extend between a proximal end 22 and a distal end 24 with a sheath lumen 26 defined along a length of the sheath 14. The sheath 14 may include a sheath hub 28 and a sheath flush port 30. The sheath hub 28 may be coupled to the proximal end 22 of the sheath 14, the sheath hub 28 including a bore (not shown) defined therein that extends co-axial with the sheath lumen 26. Further, the sheath hub 28 may incorporate a hemostasis valve 32 such that the hemostasis valve 32 may be rotated, for example, clockwise to be tightened over the treatment catheter 20 and rotated counter-clockwise to be loosened over the treatment catheter 20. Such a hemostasis valve 32 may be employed to minimize blood back-flow from a patient when the sheath 14 and the treatment catheter 20 are positioned within a patient's vascular system.

The sheath flush port 30 may extend from the sheath hub 28 or adjacently distal of the sheath hub 28. The sheath flush port 30 may be employed to flush the sheath 14 to minimize potential air pockets and air bubbles along the sheath lumen 26 of the sheath 14. Further, such sheath flush port 30 may be employed to inject contrast into the left atrium for viewing the mitral valve. The sheath 14 may include other structural features to assist in advancing the treatment catheter 20 to the mitral valve, as known to one of ordinary skill in the art.

Now referring to the treatment catheter system 12, such treatment catheter system may include the before referenced treatment catheter 20 and a handle 34 with various actuation members associated with the handle 34. Further, the treatment catheter system 12 may be coupled to the RF energy source 16 and the controller 18. The treatment catheter 20 may extend between a distal end 36 and a proximal end 38 and define an axis 40 and a primary lumen 42 extending along a longitudinal length of the treatment catheter 20. The treatment catheter 20 may include a tubular sleeve 44 or electrode outer sleeve that also defines a tubular sleeve lumen 46 along a length thereof, the tubular sleeve 44 extending through the primary lumen 42 along the axis 40 of the treatment catheter 20. As depicted in FIG. 1A, the tubular sleeve lumen 46 may include a circular cross-sectional shape or profile, however, such profile may also be rectangular, oval, tri-lobular, or any other suitable cross-sectional profile.

Further, the treatment catheter 20 may also include a first sleeve 48 and second sleeve 50 each extending alongside each other within the tubular sleeve lumen 46 and along the length of the treatment catheter 20. The first and second sleeves 48, 50 may also be referenced as first and second electrode sleeves or first and second inner sleeves. In one embodiment, the first sleeve 48 and the second sleeve 50 may be electrically isolated from each other and may each include a respective first electrode 52 and a second electrode 54. The first and second electrodes 52, 54 may extend from a distal end of the first and second sleeves 48, 50, respectively, and be electrically coupled to the RF energy source 16. In one embodiment, the treatment catheter system 12 may operate in a unipolar mode. In another embodiment, the treatment catheter system 12 may operate in a bipolar mode.

Figure 2B:
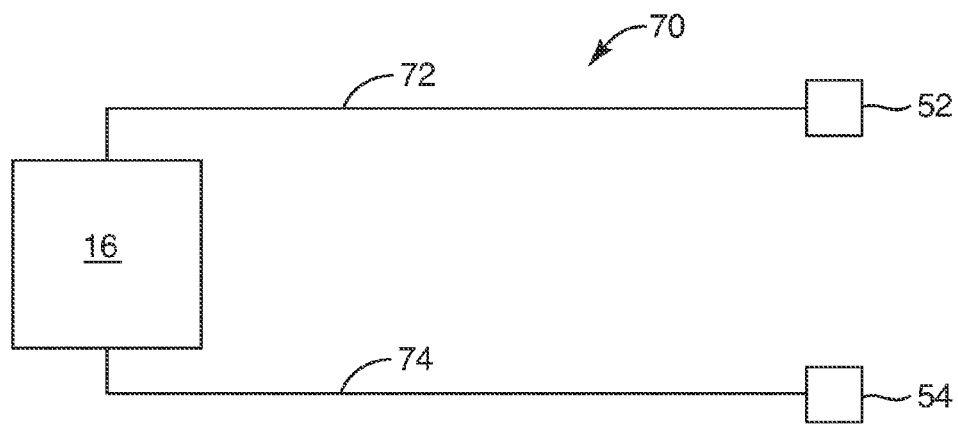
FIG. 2B is a schematic of the RF energy source and a bipolar electrode system, according to another embodiment of the present invention.

FIGS. 2A and 2B illustrate general representations of the medical device system operating in a unipolar mode (FIG. 2A) and a bipolar mode (FIG. 2B). For example, FIG. 2A represents an electrode system 60 operating in a unipolar mode, the system 60 including at least one electrode 62, such as the first and second electrodes previously set forth or other element which can serve as an electrode, in electronic communication with an RF energy source 16A or RF generator via an electronic coupling element 64, such as a wire or electronic cable. In unipolar mode, the system includes a return electrode or ground 66. The ground 66 can be positioned on the patient's skin, or alternatively, can be a pad on which a patient rests. It will be understood that the electrode 62 can include multiple electrodes which are electrically common elements, such that RF energy can be transferred from the electrodes to the ground 66. The ground 66 can be electrically coupled to the RF energy source 16A by an electronic coupled element 68, such as a wire or electronic cable.

In bipolar mode, as illustrated in FIGS. 1 and 2B, an electrode system 70 can include the first electrode 52 electrically coupled to the RF energy source 16 or RF generator by an electronic coupling element 72, such as a wire or electronic cable, and the second electrode 54 electrically coupled to the RF energy source 16 or RF generator by an electronic coupling element 74, such as a wire or electronic cable. In this manner, RF energy can be passed between the first and second electrodes 52, 54, rather than from the electrodes to a ground, as in the unipolar mode or configuration. It will be understood in view of the disclosure provided herein that the first electrode 52, the second electrode 54, and/or electrode 62 can include one or more electrically common electrodes or elements. As known to one of ordinary skill in the art, the RF energy source 16 may be any suitable RF energy generator configured to pass RF energy to the first and second electrodes 52, 54 sufficient to heat the tissue at controlled levels. In other embodiments, rather than an RF energy source as discussed herein, the medical device system 10 may include another type of energy source for heating the tissue, such as, employing ultrasound, high frequency ultrasound, lasers, microwave, or any other suitable energy for heating the tissue.

The RF energy source 16 may modulate at various energy levels. For example, such levels may include modulating the RF energy source between 0-100 watts to heat the tissue in the range of 50-85 degrees Celsius and preferably within the range of 60-70 degrees Celsius. In one embodiment, the preferable heating of the tissue may be about 65 degrees Celsius. Dependent upon the level of RF energy applied by the RF energy source 16, such heating of tissue may be implemented over a time period in the range of about twenty seconds to five minutes. In one embodiment, the RF energy applied to the tissue may be modulated to facilitate applying the RF energy for about one minute to reach the preferred temperature ranges for heating the tissue.

Now with reference to FIG. 1, the RF energy source 16 may also be coupled to a controller 18. The controller 18 may be configured to control the RF energy applied by the RF energy source 16 based on temperature readings of the tissue receiving the RF energy. For example, the treatment catheter 20 may include one or more temperature sensors (not shown) positioned at the distal end thereof and adjacent the one or more electrodes, discussed in further detail herein. The controller 18 may be coupled to the RF energy source 16 and to the one or more temperature sensors so as to control the RF energy applied (amount and duration) to the electrodes based on the temperature readings from the tissue being treated. In this manner, the controller 18 associated with the RF energy source 16 may assist in controlling the RF energy source 16 to ensure the tissue is heated to the desired temperature without overheating the tissue of the valve.

Figure 3:
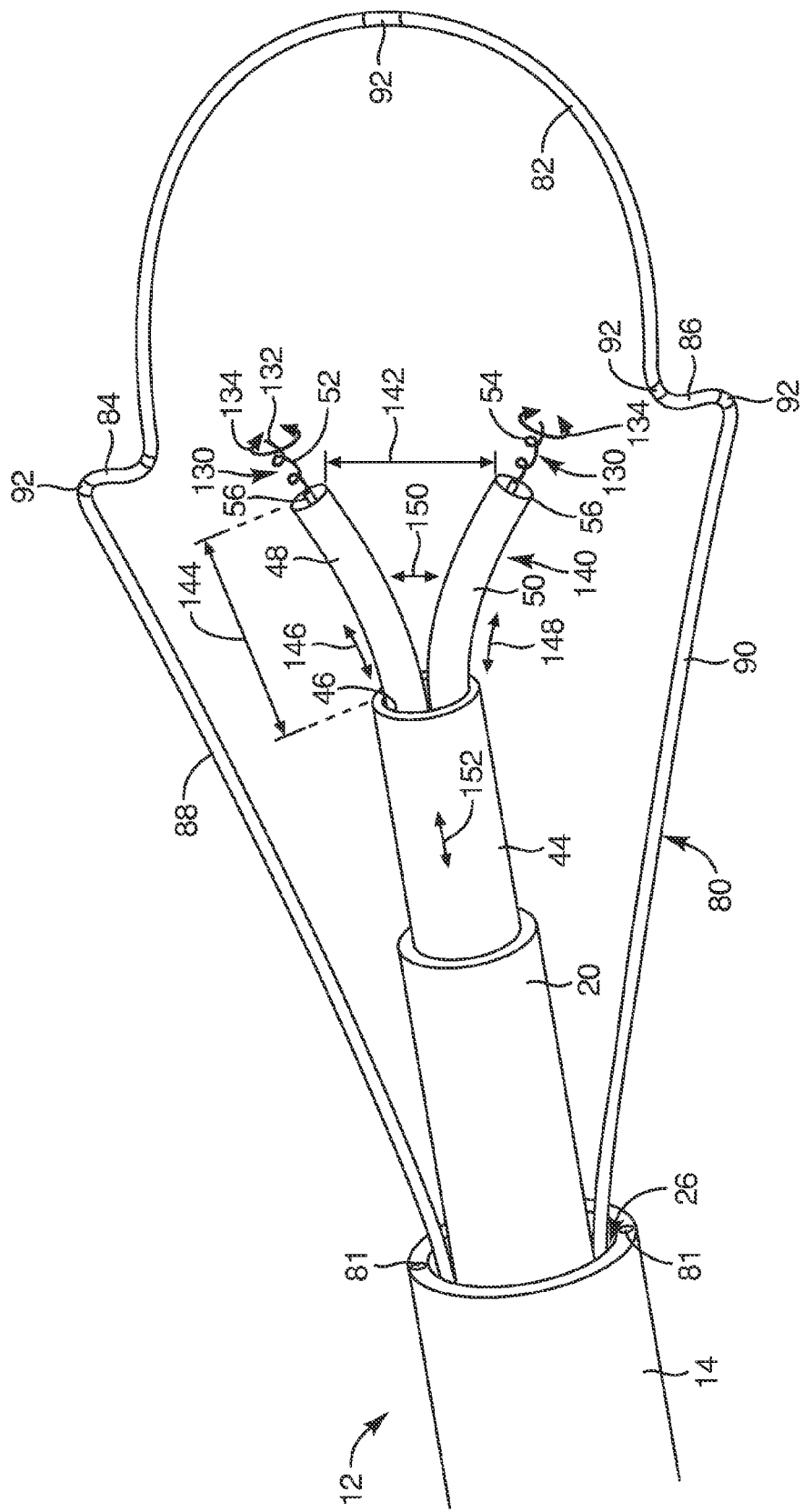
FIG. 3 is a perspective view of a distal portion of the medical device system, depicting the distal portion of a sheath, an imaging member, and a treatment catheter, according to another embodiment of the present invention.

Referring now to FIGS. 1 and 3, various components of the medical device system 10 will now be discussed in greater detail. In one embodiment, the medical device system 10 may include an imaging member 80 or imaging loop. The imaging member 80 may be advanced through the sheath lumen 26 prior to advancing the treatment catheter 20 therethrough. In another embodiment, the imaging member 80 may be advanced through peripheral lumens 81 defined in and extending longitudinally through the wall of the sheath 14. In another embodiment, the imaging member 80 may be disposed within peripheral lumens defined in the wall of the treatment catheter 20 so that the imaging member 80 is advanced simultaneously with the treatment catheter 20.

The imaging member 80 may be sized and configured to self-orient and be positioned within a valve, such as a mitral valve, shown in detail hereafter. The imaging member 80 may be in the form of a wire or a coil or the like. The imaging member 80 may be sized and configured to be constricted within the sheath 14 for advancing therethrough and, once exposed from a distal end 24 of the sheath, may self-expand to a preformed shape at a distal portion of the imaging wire 80. The preformed portion or distal portion of the imaging member 80 may include a head portion 82 and first and second shoulder portions 84, 86. For example, the head portion 82 may include a dome shaped profile with proximal ends of the head portion 82 each extending to the respective first and second shoulder portions 84, 86. The first and second shoulder portions 84, 86 may extend laterally outward relative to the proximal ends of the head portion 82. From the first and second shoulder portions 84, 86, the imaging member 80 may include first and second extensions 88, 90 that are sized and configured to extend proximally toward and through the sheath lumen 26 defined in the sheath 14. The head portion 82 and the first and second shoulder portions 84, 86 may be configured to be planar or disposed in a common plane so as to resist out-of-plane movement, but also be readily able to flex inward and outward within the plane of the imaging member 80 to compensate for the various sizes of mitral valves. Other suitable configurations may also be employed that will self-center or self-orient within a given valve to provide a physician information utilizing imaging techniques, such as the orientation, sizing, and depth of the valve being treated.

The imaging member 80 may be formed from a metallic or polymeric material, such as a super-elastic material that is suitable for constriction within the sheath 14 and self-expands once exposed from the sheath 14. In the case of a super-elastic metallic material, such as Nitinol, the head and shoulder portions of the imaging member 80 may be formed utilizing, for example, heat-setting techniques at particular temperatures in, for example, a sand bath or salt bath as known to one of ordinary skill in the art. The imaging member 80 may also be formed of a polymeric material or the combination of polymeric and metallic materials, formed as a braid or coil or utilizing machining/laser cutting techniques to form various portions of the imaging member 80 to hold structural characteristics of varying flexibility, as known to one of ordinary skill in the art.

The imaging member 80 may also include a radiopaque material. Such radiopaque material holds a material density to facilitate viewing the imaging member utilizing imaging techniques, as known in the art, as the imaging member is advanced through the sheath, deployed, and positioned within a given valve. The imaging member may include markers 92 at key locations along, for example, the head portion 82 and/or first and second shoulder portions 84, 86. In another embodiment, the imaging member 80 may include a coating or layer of radiopaque material over both the head portion 82 and the first and second shoulder portions 84, 86, and any other desired portions of the imaging member 80. In another embodiment, the imaging member 80 may include radiopaque markers 92 at key locations as well as a radiopaque coating formed as a thin layer over portions of the imaging member 80. Any suitable highly dense radiopaque material may be employed, such as, titanium, tungsten, barium sulfate, and zirconium oxide, platinum, platinum iridium, tantalum and/or combinations thereof.

As previously set forth, the treatment catheter system 12 may include the handle 34 coupled to the treatment catheter 20, the treatment catheter 20 including each of the tubular sleeve 44, and first and second sleeves 48, 50 disposed therein. The proximal end 38 of the treatment catheter 20 may be fixedly coupled to and within a bore (not shown) of the handle 34. The handle 34 may include a fluid flush port 94 for flushing the treatment catheter 20 of any air bubbles or air pockets within the treatment catheter 20 and handle 34, as known in the art. Further, the handle 34 may include a steering actuator 96, an engaging switch 98, and an electrode actuation system 100, each serving one or more functions in controlling or actuating various portions of the treatment catheter 20, tubular sleeve 44, first and second sleeves 48, 50, and/or the first and second electrodes 52, 54.

Referring to FIGS. 1 and 1A, for example, the steering actuator 96 may be in the form of a joy-stick. The steering actuator 96 may be sized and configured to manipulate a distal portion of the treatment catheter 20 so as to facilitate orienting the distal end 36 of the treatment catheter 20 in a direction adjacent to a tissue region to be treated at, for example, a mitral valve. In one embodiment, the steering actuator 96 may be coupled to one to four lines or wires extending to a distal portion of the treatment catheter 20, or any number of suitable lines to effect steering the distal portion of the treatment catheter 20. For example, the steering actuator 96 may include two pair of lines or wires or more extending longitudinally from the handle 34 and through peripheral lumens 106 defined in the wall of the treatment catheter 20. Each pair of lines may longitudinally extend through the peripheral lumens 102 along opposing sides of the wall so as to manipulate movement of a distal portion of the treatment catheter 20. For example, a first pair of lines 104 may manipulate the distal portion of the treatment catheter 20 in a first plane 108. Likewise, a second pair of lines 106 may manipulate the distal portion of the treatment catheter 20 in a second plane 110. With this arrangement, the distal portion of the treatment catheter 20 may be steered (or moved to an arcuate orientation) along the first and second planes 108, 110 as well as a combination of the first and second planes 108, 110 so as to activate two adjacent lines from the first and second pair of lines 104, 106 to steer the distal portion of the treatment catheter 20 to an arcuate orientation extending between the first and second planes 108, 110.

In one embodiment, the distal portion of the treatment catheter 20 may be sized and configured with a lower durometer than other portions of the treatment catheter 20 such that the distal portion has a greater flexibility than the other portions of the catheter 20. Such greater flexibility may readily facilitate moving and steering the distal portion of the treatment catheter 20 in various arcuate positions. The steering actuator 96 may include the joy-stick configuration such that the joy-stick extends orthogonal relative to the axis 40 of the treatment catheter 20, as depicted. In another embodiment, the joy-stick may extend with an orientation parallel, transversely alongside, or co-axial with the axis 40 of the treatment catheter 20. Other configurations and structures for the steering actuator may also be employed that are inherently intuitive for controlling the orientation of the distal portion of the treatment catheter 20.

Now with reference to FIG. 1, the engaging switch 98 at the handle 34 may be disposed directly on the handle. Further, the engaging switch 98 may be moved between an engagement position and an open position. In the engagement position, the various components/functions of the electrode actuation system 100 may be locked from linear and/or rotational movement. On the other hand, in the open position, the components of the electrode actuation system 100 may be operated for linear and/or rotational movement. In one embodiment, the engaging switch 98 may be actuated by moving the switch distally or proximally between the engagement position and the open position, respectively. In another embodiment, the engaging switch 98 may be depressed to the open position and include a spring bias to automatically move the engaging switch 98 to the closed position upon removing downward pressure to the engaging switch 98. In another embodiment, the handle 34 may include a plurality of engaging switches for controlling actuation of the various components of the electrode actuation system 100.

With respect to FIGS. 1 and 3, the electrode actuation system 100 may include a primary actuation member 112 and first and second sleeve actuation members 114, 116. The primary actuation member 112 may extend proximally from the handle 34 and may include an actuation shaft 118 and a knob 120 coupled to a proximal end of the actuation shaft 118. The actuation shaft 118 may be tubular and may be fixedly coupled to the tubular sleeve 44 disposed within the primary lumen 42 of the treatment catheter 20. Upon moving the engaging switch 98 to the open position, the primary actuation member 112 may be moved proximally and distally to actuate the tubular sleeve 44 and the first and second sleeves 48, 50 in corresponding proximal and distal directions relative to the treatment catheter 20. Further, the primary actuation member 112 may be rotated, via the knob 120, to translate common or simultaneous rotational movement of each of the tubular sleeve 44 and the first and second sleeves 48, 50. Further description as to the purpose and functionality of the primary actuation member 112 will be discussed hereafter.

The first and second sleeve actuation members 114, 116 may extend proximally from the knob 120 of the primary actuation member 112. Each of the first and second sleeve actuation members 114, 116 may include respective first and second tubular members 122, 124 and respective first and second knobs 126, 128 coupled to respective proximal ends of the first and second tubular members 122, 124. Further, the first and second sleeve actuation members 114, 116 may correspond with the first and second sleeves 48, 50 and their respective first and second electrodes 52, 54. Upon moving the engaging switch 98 to the open position (or any additional corresponding engaging switch), the first and second sleeve actuation members 114, 116 may be independently moved linearly in proximal and distal directions to translate corresponding independent linear movement to the first and second sleeves 48, 50 disposed in the treatment catheter 20. Such linear movement of the first and second sleeves 48, 50 may be relative to the tubular sleeve 44 and/or the treatment catheter 20. Further, the first and second knobs 126, 128 of the respective first and second sleeve actuation members 114, 116 may be independently rotated to translate independent rotational movement (clockwise or counter clockwise) of the respective first and second electrodes 52, 54. Such rotational movement of the first and second electrodes 52, 54 may be relative to the first and second sleeves 48, 50. Furthermore, the first and second knobs 126, 128 may each include a switch (not shown) to effect independent linear movement (distally and proximally) of the respective first and second electrodes 52, 54 relative to the first and second sleeves 48, 50. In this manner, the first and second electrodes 52, 54 may be independently controlled with rotational and linear movement.

Now with reference to FIG. 3, the first and second electrodes 52, 54 may each include a helical configuration 130 at a distal end portion thereof. Further, each helical electrode may include a pointed distal end 132. The first and second electrodes 52, 54 may be configured to contact and extend into tissue of the valve. With the helical configuration of the first and second electrodes 52, 54, the rotational movement (as indicated by dual rotational arrow 134) transferred to the first and second electrodes 52, 54 via the first and second knobs 126, 128 at the handle 34 (see FIG. 1), facilitates the first and second electrodes 52, 54 to twist or sink into the tissue of a valve and be secured thereto. Likewise, rotational movement (in the opposite direction) of the first and second electrodes 52, 54 readily facilitates withdrawing the helical configuration of the first and second electrodes 52, 54 from the tissue of the valve. Further, such pointed distal end 132 of each of the helical electrodes may facilitate ready insertion into the tissue.

Figure 3A:
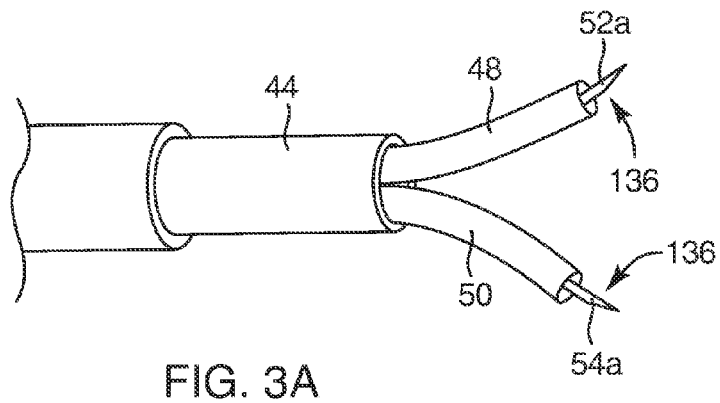
FIG. 3A is a perspective view of another embodiment of the distal portion of a treatment catheter, depicting the electrodes having a needle configuration, according to the present invention.

Referring to FIG. 3A, in another embodiment, the first and second electrodes 52a, 54a may include a needle configuration 136 with a pointed distal end 138. In other words, the needle configuration 136 of the distal portion of the first and second electrodes 52a, 54a extends in a substantially linear manner relative to the orientation of the first and second sleeves 48, 50. With this arrangement, insertion of the first and second electrodes 52a, 54a into tissue may be employed with linear movement translated from the first and second sleeve actuation members 114, 116 at the handle 34 (see FIG. 1). Further, the first and second electrodes 52a, 54a may be linearly moveable relative to the first and second sleeves 48, 50 such that the functionality of the first and second sleeves 48, 50, as well as the tubular sleeve 44, may be substantially similar to the previous embodiment. In still another embodiment, the first and second electrodes 52, 54 may include a limited helical configuration with only, for example, a half or up to one turn in the helical configuration. In another embodiment, rather than the needle configuration 136, the first and second electrodes may include an atraumatic surface with, for example, a blunt end such that the first and second electrodes are configured to make contact with the tissue at the valve, but do not puncture (or go into) the tissue of the valve.

In another embodiment, similar to the embodiments of FIGS. 3 and 3A, the first and second sleeve members 48, 50 may each house and include a needle portion and a loop portion. The needle portion may be extendable through an axis of the loop portion. The loop portion may include one or more loops or spirals that may be spaced from and extend around the needle portion. In one embodiment, the loop portion may include a helical structure with spirals that radially taper toward the distal end or, otherwise said, the radius of the loops or spirals decrease toward the distal end so as to have a tapered profile toward the distal end. In one embodiment, the loop portion may be an electrode and the needle portion may be a temperature sensor. In this manner, the needle portion may be linearly moved and positioned within the tissue to sense a temperature of the tissue with the loop portion making contact with the outer surface of the tissue to, thereby, receive RF energy and heat the tissue. Further, with this arrangement, the loop portion may contact a larger surface area of the tissue, than the electrodes described in the other embodiments herein, for heating the tissue with the needle portion positioned in the tissue and sensing the temperature of the heated tissue. In this embodiment, the needle portion and loop portion may be separate distinct elements such that they are independently linearly moveable relative to each other. In another embodiment, the needle portion and loop portion may be coupled together (or operatively coupled together along the length of first and second sleeves or handle) so that the needle portion and loop portion linearly move together, but are independently linearly moveable relative to the other one of the electrodes of the splayed first and second sleeves 48, 50.

Figure 3B:
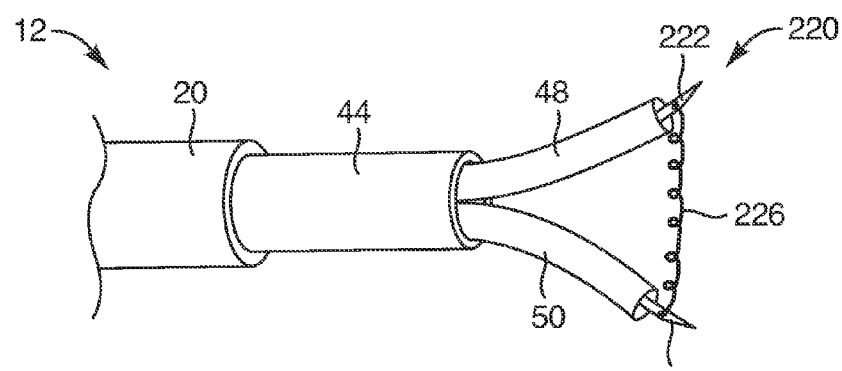
FIG. 3B is a perspective view of another embodiment of the distal portion of a treatment catheter, depicting a portion of a unipolar electrode system, according to the present invention.

With respect to FIG. 3B, in another embodiment, the treatment catheter system 12 may be configured to operate in a unipolar mode, similar to that previously set forth and described relative to FIG. 2A. For example, the treatment catheter 20 may include at least one electrode 220 having a first needle portion 222 and a second needle portion 224 with a conductive element 226, such as a conductive coil, extending therebetween. The first and second needle portions 222, 224 of the at least one electrode 220 may include similar functionality as that described in other embodiments herein, e.g., independent linear movement relative to the first and second sleeves 48, 50. Likewise, the first and second sleeves 48, 50 as well as the tubular sleeve 44 may include similar functionality as that described in the other embodiments herein. With this arrangement, the unipolar mode of an electrode system may be employed with the treatment catheter system 12. Further, in this embodiment, the first and second sleeves 48, 50 may each include a temperature sensor (not shown) associated with its respective sleeve and/or associated with the first needle portion 222 and the second needle portion 224 so as to sense and provide the temperature of the tissue being heated by the at least one electrode 220.

Referring back to FIG. 3, as previously set forth, the first and second electrodes 52, 54 may be electrically isolated within lumens extending along the length of the first and second sleeves 48, 50 disposed within the treatment catheter 20. Further, the first and second sleeves 48, 50 and their respective first and second electrodes 52, 54 may be independently moved relative to each other, as indicated with first and second bi-directional arrows 146, 148. In other words, the first and second sleeve 48, 50 may be moved independently, distally or proximally, relative to the tubular sleeve 44 and/or the treatment catheter 20.

In another embodiment, the distal portion of the first and second sleeves 48, 50 may be moved simultaneously between a constricted or constrained position and one or more exposed or expanded positions with movement of the tubular sleeve 44 relative to the first and second sleeves 48, 50, as indicated by bi-directional arrow 152. In the constricted position, the distal portion of each of the first and second sleeves 48, 50 extend substantially linear or substantially parallel to each other as they are positioned within the tubular sleeve lumen 46 of the tubular sleeve 44. In the exposed position, the first and second sleeves 48, 50 are deployed from the tubular sleeve 44 and/or the treatment catheter 20. In one embodiment, the first and second sleeves 48, 50 may be biased away from each other, as indicated by arrow 150, so as to splay laterally outward. Such splayed condition of the first and second sleeves 48, 50 may be such that the distal portion of the first and second sleeves 48, 50 maintain a substantially planar position in both the constricted and exposed or expanded positions. Further, such distal portion of the first and second sleeves 48, 50 may extend from the tubular sleeve 44 in a v-configuration 140, or Y-configuration, or the like.

In one embodiment, the first and second sleeves 48, 50 may each include one or more rods (not shown) embedded in the wall of the first and second sleeves 48, 50 or, alternatively, adhesively attached to a wall surface of the first and second sleeves 48, 50. In a relaxed state, the one or more rods may include a bend or curvature and be positioned on the first and second sleeves 48, 50 such that, when in the constricted position, the first and second sleeves are biased laterally outward and, when in the exposed position, the first and second sleeves 48, 50 splay laterally away from each other. With this arrangement, the distal portion of the first and second sleeves 48, 50 may be biased away from each other.

Further, in another embodiment, a lateral distance 142 between distal ends of the first and second sleeves 48, 50 may be calculated and determined relative to a length 144 by which the distal end of the tubular sleeve 44 is withdrawn from the distal ends of the first and second sleeves 48, 50. That is, the lateral distance 142 between the distal ends of the first and second sleeves 48, 50 is a function of or dependent upon the length 144 by which the tubular sleeve 44 is withdrawn. In this manner, the lateral distance 142 between the electrodes may be predetermined and further, may be enlarged or minimized to multiple predefined or predetermined lateral distances 142. The advantages for a physician to vary the lateral distance 142 between the splayed distal ends of the first and second sleeves 48, 50 will be understood in view of the disclosure provided herein relative to heating tissue regions of the valve.

As previously set forth, the distal end portion of the treatment catheter system 12 may include one or more temperature sensors. In one embodiment, each of the first electrode 52 and the second electrode 54 may include a temperature sensor 56 associated therewith. For example, the temperature sensor 56 may be positioned at a base (or proximal) of the helical configuration of each of the first and second electrodes 52, 54. In another embodiment, the temperature sensor may be positioned at a distal end of each of the first and second sleeves 48, 50. In another embodiment, the temperature sensor 56 may be associated with the helical structure of the electrode itself. The temperature sensor 56 positioned adjacent to the first and second electrodes 52, 54 may be coupled to the controller 18 via respective electronic elements 58, 59, such as wires (see FIG. 1).

Figure 3C:
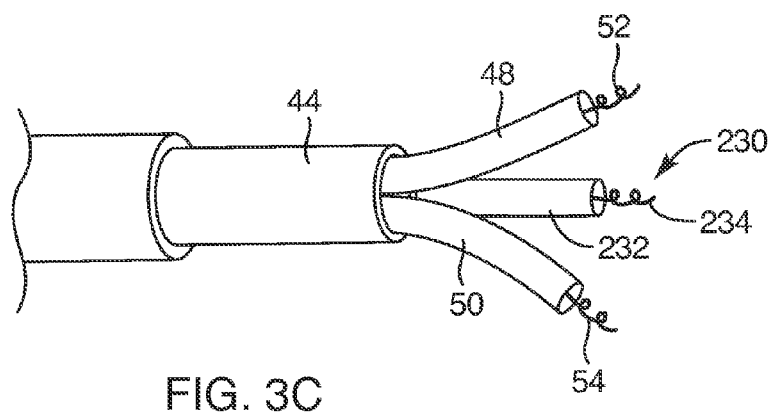
FIG. 3C is a perspective view of another embodiment of a distal portion of a treatment catheter, depicting a temperature sensor positioned between two electrodes, according to the present invention.

With respect to FIG. 3C, in another embodiment, a temperature sensor 230 may be disposed within and moveable to extend from a third sleeve 232. The third sleeve 232 may be positioned between the splayed first and second sleeves 48, 50 that house the first and second electrodes 52, 54. The temperature sensor 230 associated with the third sleeve may be in addition to (or instead of) the temperature sensors 56 (FIG. 3) associated with the first and second sleeves 48, 50.

The third sleeve 232 may be independently moveable in a linear direction (distally and proximally) relative to the first and second sleeves 48, 50 and/or the tubular sleeve 44. Further, the temperature sensor 230 may be independently linearly moveable relative to the third sleeve 232. Furthermore, the temperature sensor 230 may be associated with or include a helical structure 234 that may be rotated to twist into tissue between the first and second electrodes 52, 54. In this manner, the temperature sensor 230 may sense the temperature of the tissue being heated between the first and second electrodes 52, 54 and transmit such temperature to the controller 18 to control the RF energy being applied to the tissue, similar to that depicted and discussed relative to FIGS. 1 and 3. Further, the handle of the embodiment depicted in FIG. 3C may include a third sleeve actuator member (not shown) similar to the first and second sleeve actuator members 114, 116 depicted in FIG. 1 so as to facilitate linear and rotational movement of the third sleeve 232 and the temperature sensor 230. Furthermore, as can be appreciated, such third sleeve actuator member may include an electronic element (not shown) coupling the temperature sensor 230 to the controller 18.

In another embodiment, the temperature sensor 230 extending from the third sleeve 232 may be associated with or include a needle configuration. In another embodiment, the temperature sensor 230 extending from the third sleeve 232 may be associated with or include a flat surface that is atraumatic and sized and configured to contact the outer surface of the tissue between the first and second electrodes 52, 54 to sense the temperature thereof. The temperature sensors disclosed herein may be any suitable type of temperature sensor known to one of ordinary skill in the art, such as a thermocouple or thermistor.

In another embodiment, the third sleeve 232 may be sized and configured to house a third electrode similar to the first and second sleeves 48, 50 and their respective first and second electrodes 52, 54 such that the third electrode may include the helical structure as depicted in FIG. 3C. Further, in this embodiment, the third sleeve may include a temperature sensor associated therewith or the temperature sensor may be associated with the electrode itself similar to the previous embodiments. In this embodiment, the handle 34 would include an associated third sleeve actuator member similar to the first and second sleeve actuator members 114, 116 and lines or conductive elements extending to the controller 18 as well as the RF energy source 16, similar to that depicted in FIG. 1.

With respect to FIGS. 1 and 3, generally, medical grade metals, metal alloys, plastics, polymers, synthetics may be used to fabricate the medical device system 10 including the sheath 14, the treatment catheter system 12, and its associated electrode components. As known to one of ordinary skill in the art, the sheath 14 and treatment catheter 20 with its respective tubular sleeve 44, and first and second sleeves 48, 50 may be formed from a polymeric material, such as, polytetrafluoroethylene (PTFE), fluorinated ethylene propylene (FEP), high-density polyethylene (HDPE), polyether block amide (PEBA), nylon, polyimide, polyamide, or any other suitable polymeric material, as well as may include metallic/polymeric coils, braids, and various sealing rings, and metallic components and fasteners for coupling the various components of the medical device system 10. Such components may be formed using various manufacturing techniques, such as extrusion, thermal reflowing, braiding, etc., or any other manufacturing technique as known by one of ordinary skill in the art. The electrodes 52, 54 may be made of a metallic material, such as stainless steel, platinum iridium, mp35, mp35 n-lt, silver, tungsten, tantalum, drawn filled tubing (DFT) or combinations thereof, as known in the art. The handle 34 and its various components may be formed of plastic and metallic materials, various sealing rings, fasteners, etc., that may be machined or formed with various molding techniques, as known to one of ordinary skill in the art.

With respect to FIGS. 4 through 10, implementation of the medical device system, according to one embodiment, will now be described relative to, for example, the mitral valve 170 in the heart 160. As previously set forth, the medical device system of the present invention is generally configured to non-invasively and percutaneously treat valves to minimize and/or prevent valve regurgitation or valve prolapse and may be implemented with any of the valves in the heart.

Figure 4:
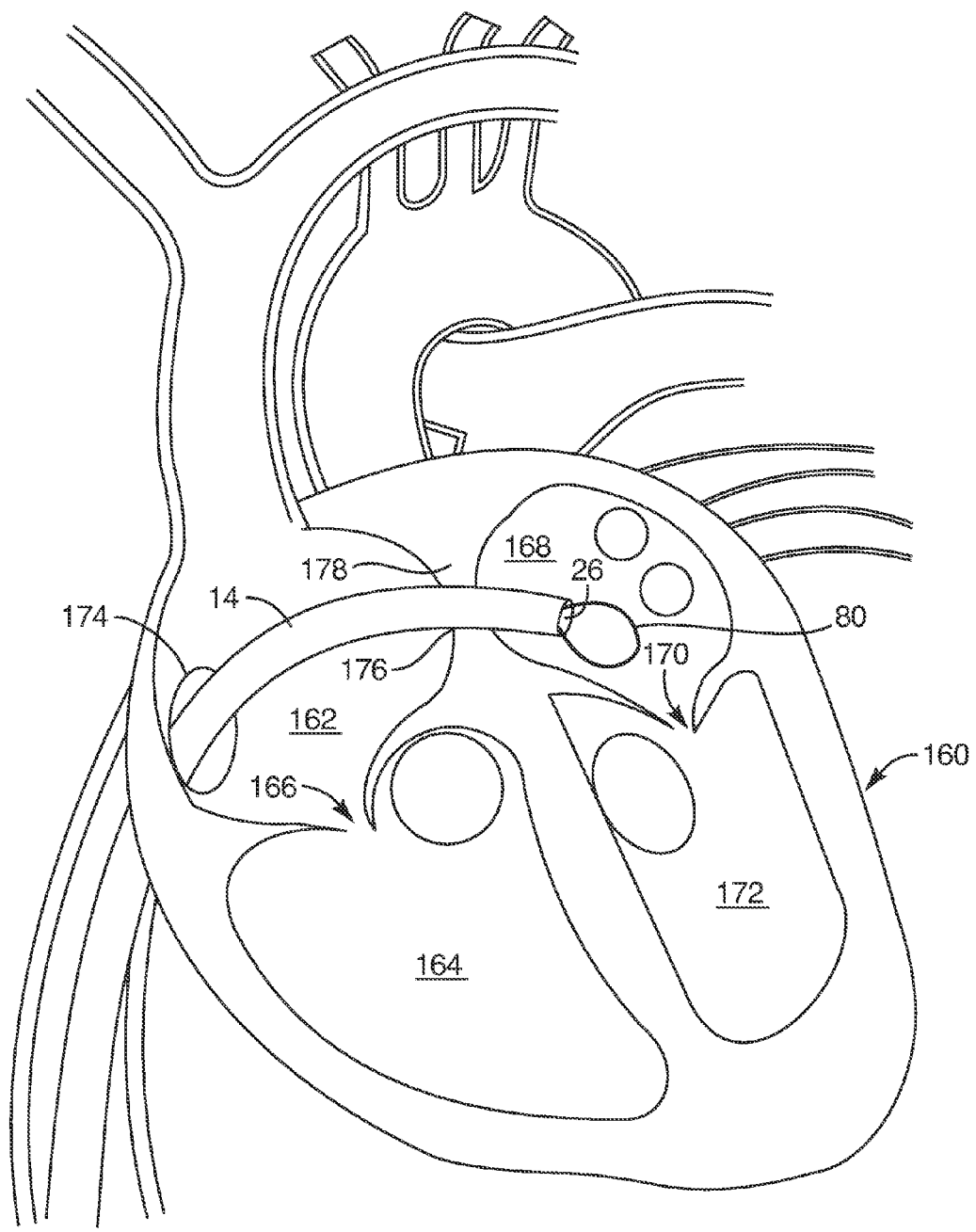
FIG. 4 is a cross-sectional view of a heart, depicting a partially deployed imaging member extending from a sheath advanced through a septum of the heart, according to another embodiment of the present invention.

FIG. 4 is a general representation of the heart 160 and its circulatory system, depicting the four chambers of the heart, namely, the right atrium 162 and the right ventricle 164 with the tricuspid valve 166 therebetween and the left atrium 168 and the left ventricle 172 with the mitral valve 170 therebetween. In this example, the valve to be treated is the mitral valve 170. As such, access to the left atrium 168 may be employed using known techniques and procedures by a physician, such as performing a trans-septal puncture at the septum wall 178 between the right and left atria 162, 168. The physician may then advance the sheath 14 of the medial device system 10 over a wire (not shown) through the inferior vena cava 174 and then through the septum wall 178 to gain access to the left atrium 168. Once the distal portion of the sheath 14 is positioned in the left atrium 168, the imaging member 80 may be advanced through the sheath lumen 26 and deployed in the left atrium 168, FIG. 4 depicting the imaging loop 80 partially deployed in the left atrium 168 adjacently above the mitral valve 170. The physician may utilize imaging techniques to view the mitral valve 170 with, for example, flushing contrast into the left atrium 168 such that the physician can position the distal end of the sheath 14 adjacent the mitral valve 170 to fully deploy the imaging member 80 within the mitral valve 170.

Figure 5:
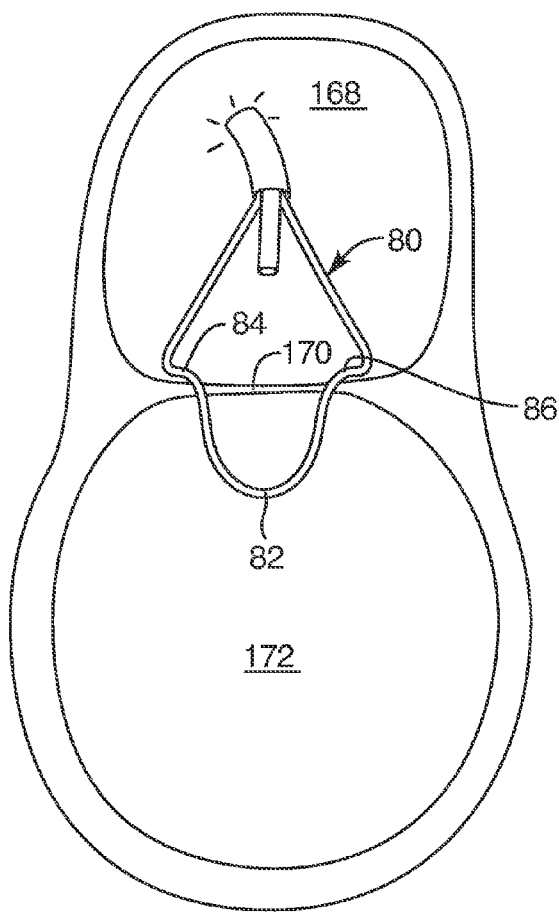
FIG. 5 is a simplified cross-sectional view of a left side of the heart, depicting the imaging member positioned in a mitral valve of the heart, according to another embodiment of the present invention.
Figure 5A:
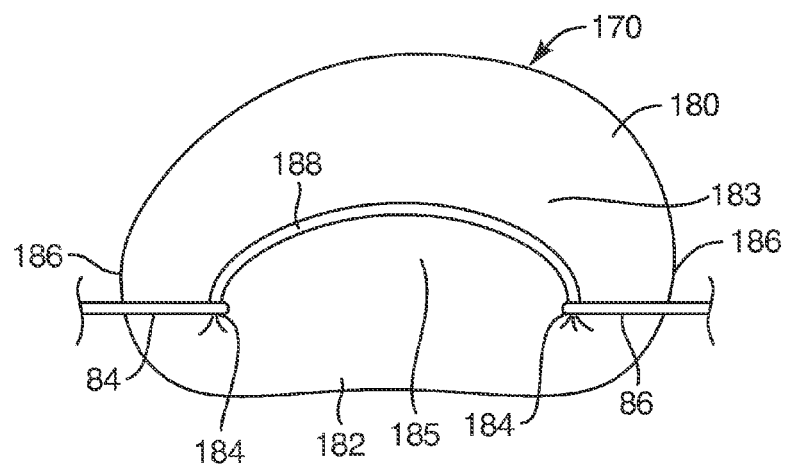
FIG. 5A is a simplified top view of the mitral valve with the imaging member positioned therein, according to another embodiment of the present invention.

FIGS. 5 and 5A depict the imaging member 80 fully deployed in the mitral valve 170, FIG. 5 depicting a simplified side view of the left atrium 168 and left ventricle 172 of the heart 160. Upon deploying the imaging member 80 within the mitral valve 170, the imaging member 80 may self-orient at corners 184 between the posterior annulus and the anterior annulus 182 of the valve 170. Once the imaging member 80 self-orients within the valve with the head portion 82 of the imaging member 80 disposed in the left ventricle 172, if the imaging member 80 has not self-seated, the physician may move the imaging member 80 distally to seat the shoulder portions 84, 86 against the outer edge 186 of the valve 170. With the imaging member 80 in the seated and oriented positions, the head portion 82 of the imaging member 80 extends into the left ventricle 172 with the first and second shoulder portions 84, 86 extending laterally from the corners 184 and over the outer edge 186 of the valve 170. FIG. 5A is a top view of the mitral valve 170 (viewed from the left atrium 168), depicting a simplified partial view of the first and second shoulder portions 84, 86 of the imaging member 80 extending laterally and resting over the outer edges 186 of the valve 170 between the posterior annulus 180 and the anterior annulus 182 of the mitral valve 170. The mitral valve 170, depicted in FIG. 5A, illustrates an example of an unhealthy enlarged mitral valve undergoing regurgitation, depicting the mitral valve 170 with a gap 188 between the posterior and anterior leaflets 183, 185 when it should be in a fully closed position.

Figure 6:
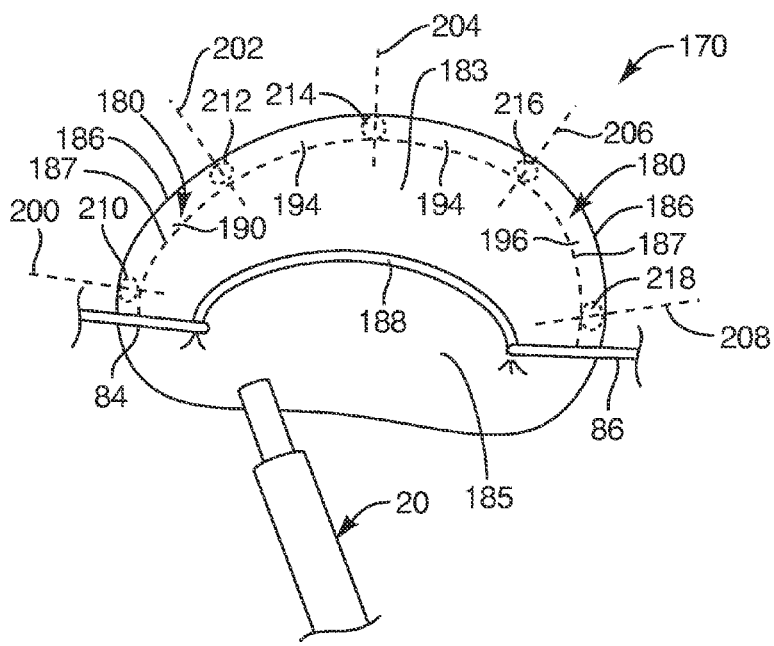
FIG. 6 is a simplified top view of the mitral valve, depicting a distal portion of a treatment catheter extending toward a first tissue region of the mitral valve, according to another embodiment of the present invention.

Now with reference to FIG. 6, upon the imaging member 80 being positioned in the mitral valve 170, the physician may obtain imaging information relative to the radiopaque markers 92 (FIG. 3) or coating associated with the imaging member 80 as well as by injecting contrast through the sheath or treatment catheter 20. Such imaging information may include various dimensions of the mitral valve 170, such as dimensions relative to the posterior annulus 180 and the posterior leaflet 183, and the anterior annulus 182 and the anterior leaflet 185, and any other features/dimension that may be ascertained and useful. In this example, the tissue of the valve to be treated is the posterior annulus 180, depicted between dashed boundary line 187 and the outer edge 186 extending between the first and second shoulder portions 84, 86 of the imaging member 80. Based on the imaging information and dimensions obtained therefrom, the physician may determine regions with associated boundaries for heating the posterior annulus 180.

For example, the posterior annulus 180 may be divided into four regions, namely, a first tissue region 190, a second tissue region 192, a third tissue region 194, and a fourth tissue region 196 each associated with respective boundary lines, namely, a first boundary line 200, a second boundary line 202, a third boundary line 204, a fourth boundary line 206, and a fifth boundary line 208. Such division of regions of the posterior annulus 180 will be for purposes of heating the tissue with the electrodes of the treatment catheter 20 attached or positioned generally along the associated boundary lines, as discussed in further detail herein. Along each boundary line associated with one or two regions of the posterior annulus 180, each boundary line may also include an associated target point (or otherwise said, a target area) at which the physician may target contacting the posterior annulus 180 with one of the first and second electrodes, namely, a first target point 210, a second target point 212, a third target point 214, a fourth target point 216, and a fifth target point 218. Depending on the dimensions of the posterior annulus 180 and other factors, such as the gap 188 of an unhealthy valve, the physician may divide the posterior annulus 180 into two or three regions or even up to five or six regions. Further factors relating to dimensioning and the number of regions to be treated may take into account the viable minimum and maximum predefined lateral distances 142 between the splayed distal ends of the first and second electrodes 52, 54 that may be readily employed relative to the dimensions of the given posterior annulus 180, as previously described relative to FIG. 3.

With respect to FIGS. 1 and 6, once the physician has obtained the desired imaging information, the physician may then advance the treatment catheter toward the first target point 210 or along the first boundary line 200 determined on the posterior annulus 180 and adjacent the first shoulder portion 84 of the imaging member 80. In addition, to assist the physician, the steering actuator 96 may be actuated to orient the distal portion of the treatment catheter 20 so as to point the distal end toward the first shoulder portion 84 of the imaging member 80.

Figure 6A:
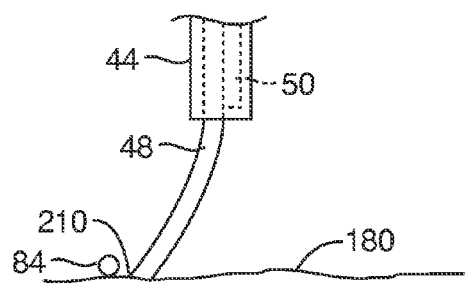
FIG. 6A is a side view of the distal portion of the treatment catheter, depicting a first sleeve positioned against the mitral valve, according to another embodiment of the present invention.
Figure 6B:
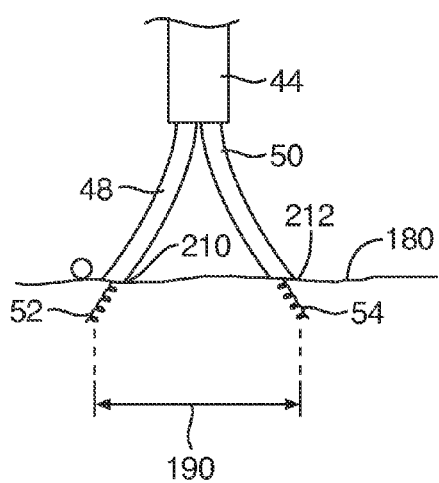
FIG. 6B is a side view of the distal portion of the treatment catheter, depicting a first sleeve and a second sleeve positioned against the mitral valve with a first and second electrode moved distally to contact the mitral valve, according to another embodiment of the present invention.

With respect to FIGS. 1 and 6A, in one embodiment, the first sleeve 48 may be moved distally relative to the tubular sleeve 44 by linearly actuating the first sleeve actuation member 114 at the handle 34 to contact the first target point 210 on the posterior annulus 180 adjacent the first shoulder portion 84 of the imaging member 80. At this stage, the second sleeve 50 may be maintained within the tubular sleeve 44. With reference to FIGS. 1 and 6B, upon contacting the posterior annulus 180 at the first target point 210, the first electrode 52 may be extended into and secured to the posterior annulus 180 by rotationally actuating the first knob 126 of the first sleeve actuation member 114 at the handle 34. Similarly, the second sleeve 54 may then be moved distally by linearly moving the second sleeve actuation member 116 at the handle 34 to contact the second target point 212 on the posterior annulus 180, after which, the second electrode 54 may be moved distally by rotating the second knob 128 at the handle 34.

With continued reference to FIGS. 1 and 6B, in another embodiment, both the first and second sleeves 48, 50 may be simultaneously exposed or moved distally relative to the tubular sleeve 44 by, for example, actuating the primary actuation member 112 at the handle 34. Such may be employed by moving the primary actuation member 112 proximally to withdraw the tubular sleeve 44 and, thereby, expose both the first and second sleeves 48, 50. As previously set forth, the first sleeve 48 may then be positioned over the first target point 210 and then attached to the posterior annulus 180 with the first electrode 52. Similarly, the second sleeve 50 may then be positioned and attached to the posterior annulus 180 at the second target point 212. Further, the attachment of the first and second electrodes 52, 54 to the posterior annulus 180 may readily be employed due to the helical configuration of the electrodes such that the electrodes may be rotated via the first and second knobs 126, 128 at the handle 34 to secure the first and second electrodes 52, 54 into the tissue of the posterior annulus 180. As such, the first and second sleeves 48, 50 may be individually deployed for contacting and securing to the posterior annulus 180 as well as the first and second sleeves 48, 50 may be simultaneously deployed from the tubular sleeve 44 for securing to the posterior annulus 180.

Figure 7:
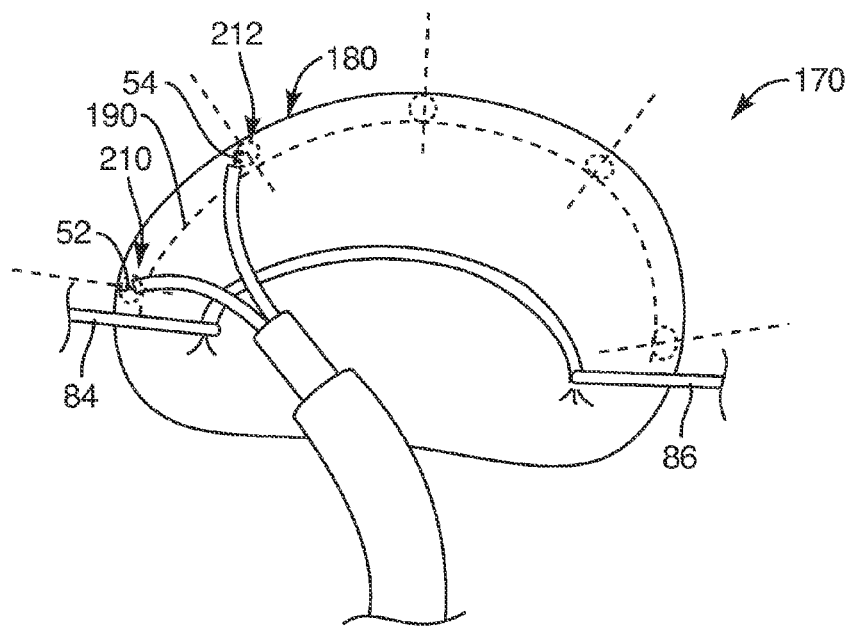
FIG. 7 is a simplified top view of the mitral valve, depicting first and second electrodes contacting the mitral valve, according to another embodiment of the present invention.

Now with reference to FIGS. 1, 6B, and 7, upon contacting or securing the first and second electrodes 52, 54 to the posterior annulus 180 at the respective first and second target points 210, 212, as depicted in FIGS. 6B and 7, the tissue between the first and second electrodes 52, 54 or a first tissue region 190 can be heated by activating the first and second electrodes 52, 54. Such heating of the tissue may be employed at predetermined RF energy levels and for a predetermined period of time. In one embodiment, the RF energy level may be modulated in the range of about 0 to 100 watts and for a period of time ranging between about twenty seconds to five minutes until the tissue is heated to a temperature in the range of approximately 50 degrees to 85 degrees Celsius. As previously set forth, the first and second electrodes 52, 54 may be activated by transmitting RF energy from the RF energy source 16 or RF generator, the RF energy source 16 being electrically coupled to the first and second electrodes 52, 54. Further, as previously set forth, the one or more temperature sensors (not shown) may transmit temperature readings of the tissue being heated to the controller 18. Once the tissue has been heated sufficiently, the controller 18 may automatically de-activate or reduce the RF energy source 16. In addition, or instead of, there may be a display for the physician to view the temperature reading so that the physician may manually de-activate the RF energy source 16 once the tissue region is sufficiently heated. With this arrangement, the tissue may be heated to ensure sufficient heating of the tissue as well as to minimize over heating the tissue at the valve 170. Such activation and de-activation of the RF energy source 16 may be at a switch on the housing of the RF energy source or at a foot pedal coupled to the RF energy source 16 or on the handle 34 of the treatment catheter system 12.

Figure 7A:
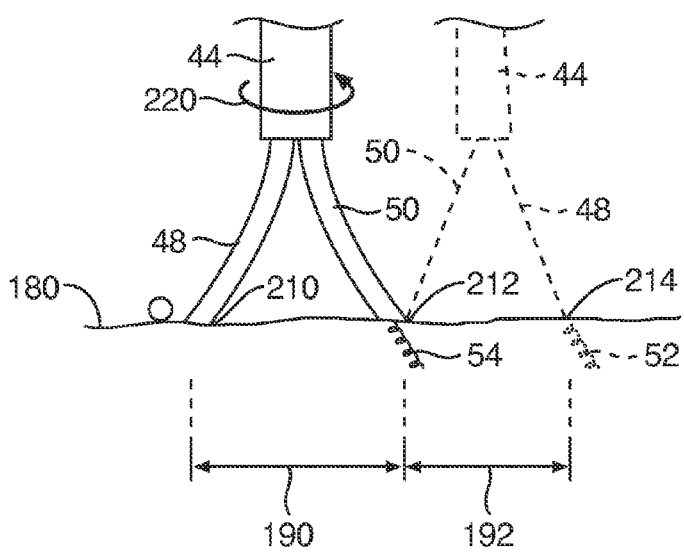
FIG. 7A is a side view of the distal portion of the treatment catheter, depicting the treatment catheter pivoting about the second sleeve, according to another embodiment of the present invention.

With respect to FIGS. 1 and 7A, upon treating the tissue at the first tissue region 190 with RF energy, the first electrode may be withdrawn from the tissue and into the first sleeve 48 by rotating the first knob 126 of the first sleeve actuation member 114 at the handle 34. The first sleeve 48 may now be moved from the first target point 210 to the third target point 214 defined along the third boundary line 204 (FIG. 6) defined on the posterior annulus 180 to treat a second tissue region 192. Movement of the first sleeve 48 to the third target point 214 may be employed by rotating the tubular sleeve 44 about 180 degrees, as indicated by rotational arrow 220, by rotating the knob 120 of the primary actuation member 112 at the handle 34 while the second electrode 54 maintains its secured position at the second target point 212 on the posterior annulus 180. With this arrangement, the tubular sleeve 44 and the first and second sleeves 48, 50 rotate and, more particularly, pivot about the second sleeve 50 with the second electrode 54 maintaining its position in the tissue. Once the tubular sleeve 44 and first and second sleeves 48, 50 are pivoted with the first sleeve 48 positioned at the third target point 214 (as depicted in outline form in FIG. 7A), the first electrode 52 may be secured to the tissue of the posterior annulus 180 at the third target point 214 by rotating the first knob 126 to distally extend the first electrode 52 into the tissue. In one embodiment, the primary actuator member 112 may be rotated to rotate the tubular sleeve 44 as well as the first and second sleeves 48, 50 in a clockwise and counter-clockwise direction with free rotation. In another embodiment, the primary actuator member 112 may include a mechanism to limit or control the amount of rotation of the tubular sleeve 44 and the first and second sleeves 48, 50. For example, the mechanism for controlling such rotation may be limited to a full turn or angle of rotation of 360 degrees in both the clockwise and counter-clockwise directions. In another embodiment, the mechanism for controlling such rotation may be limited to the range of 110 to 250 degrees and, further, within the range of 135 degrees and 225 degrees in both the clockwise and counter-clockwise directions.

Figure 8:
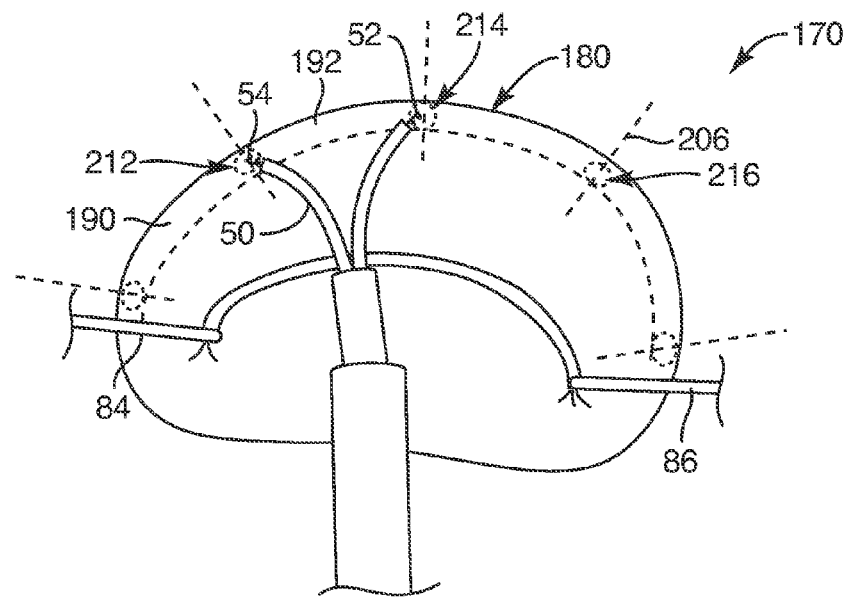
FIGS. 8, 9 and 10 are a simplified top views of the mitral valve, depicting the first and second electrodes positioned to heat respective second, third, and fourth tissue regions, according to another embodiment of the present invention.
Figure 9:
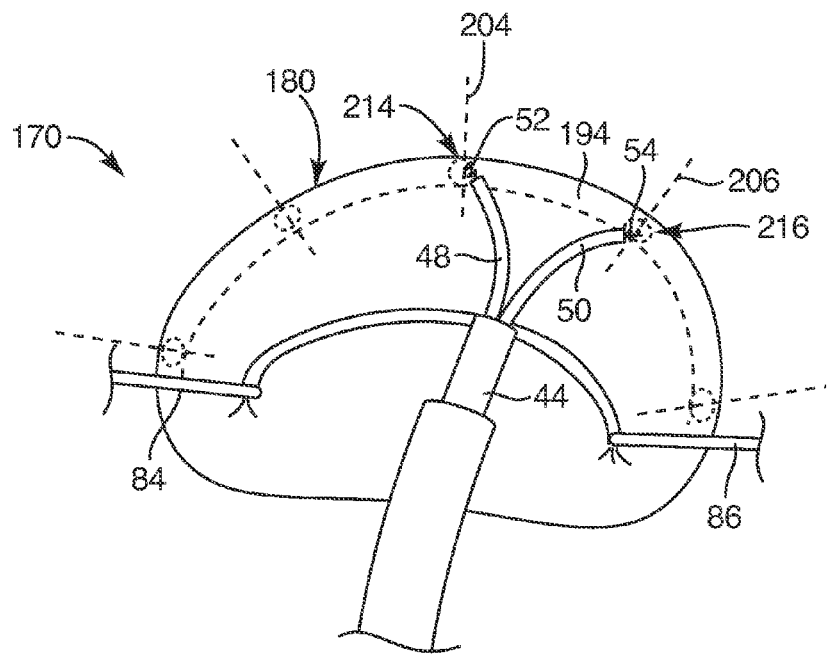
Figure 10:
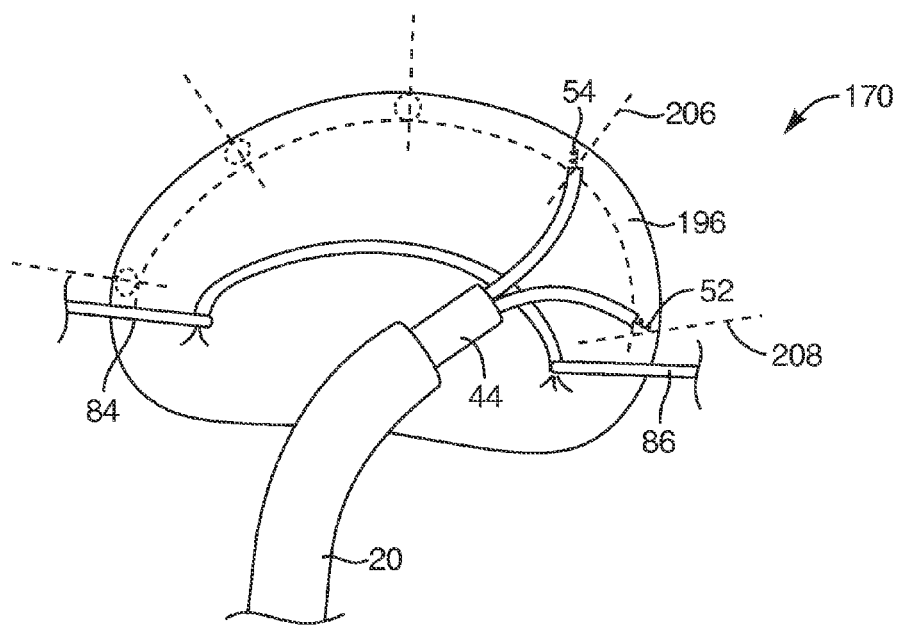

Now with reference to FIGS. 8, 9, and 10, similar steps may be employed to that previously described to heat the remaining tissue regions. For example, as depicted in FIG. 8, the first and second electrodes 52, 54 are secured to the tissue of the posterior annulus 180 with a second tissue region 192 therebetween. As such, the tissue of the second tissue region 192 may then be heated with RF energy, similar to that previously set forth for the first tissue region 190.

With respect to FIGS. 8 and 9, once the second tissue region 192 has been sufficiently heated, the second electrode 54 may be withdrawn from the tissue so that the tubular sleeve 44 (as well as the first and second sleeves 48, 50) may rotate to pivot about the first sleeve 48 with the first electrode 52 maintaining its position in the tissue. The pivoted second sleeve 50 may then be positioned at the fourth target point 216 along the fourth boundary line 206 (similar to the process described and depicted in FIG. 7A). The second electrode 54 may then be rotated and secured to the fourth target point 216. As such, once the tubular sleeve 44 is pivoted and the second electrode 54 secured to the tissue proximate the fourth boundary line 206 at the fourth target point 216, as depicted in FIG. 9, the tissue between the first and second electrodes 52, 54 may be heated to treat the third tissue region 194. With respect to FIGS. 9 and 10, once the third tissue region 194 has undergone heat treatment, the first electrode 52 may be withdrawn from proximate the third boundary line 204 so that the tubular member 44 may be rotated to move the first sleeve 48 to the fifth boundary line 208 so as to pivot about the second sleeve 50, similar to that previously described. The first electrode 52 may then be secured proximate to the fifth boundary line 208 so that the tissue in the fourth tissue region 196 may be heat treated, as depicted in FIG. 10.

Figure 11:
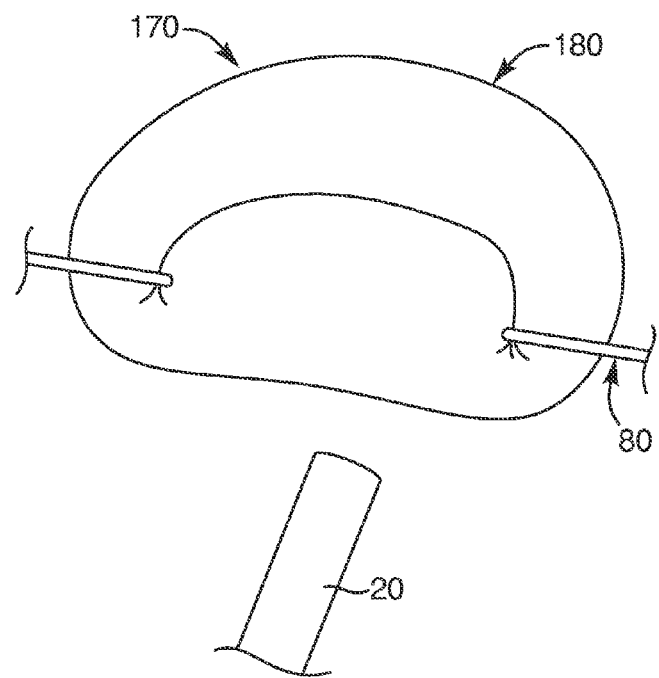
FIG. 11 is a simplified top view of the mitral valve, depicting the treatment catheter withdrawn from the mitral valve, according to another embodiment of the present invention.

With respect to FIGS. 10 and 11, once the fourth tissue region 196 has been treated with RF energy, the first and second electrodes 52, 54 may be withdrawn from the tissue and into the respective first and second sleeves 48, 50 and the tubular sleeve 44 may be moved proximally into the treatment catheter 20. The physician may now view the mitral valve and assess whether there has been ample tissue shrinkage so as to restore the valve to proper function. Due to the high collagen content of the tissue at the mitral valve 170, the tissue shrinking effects are almost immediate and, thus, the physician may determine whether the procedure was successful or if additional tissue regions for heating should be implemented. Once the physician is satisfied that the valve has been restored to healthy valve function, the physician may then withdraw and remove the treatment catheter 20, imaging member 80, and sheath 14 from the heart and vascular system of the patient.

Advantageously, the denatured collagen in the tissue resulting from heating the tissue with RF energy is absorbed and replaced with new collagen over a minimal period of time. As such, if in the future the valve digresses and the mitral regurgitation condition returns, the physician can readily again perform the same procedure set forth herein to treat the valve with RF energy to, thereby, modify the geometry of the mitral valve and again restore proper function to the valve.

Now referring to FIGS. 12, 12A, 13 and 14, another embodiment of a medical device system 240 for treating a valve is provided. With respect to FIGS. 1, 12 and 12A, the medical device system 240 of this embodiment may include the sheath 14, the imaging member 80, the treatment catheter 20 and handle 34. Rather than the first and second sleeves and the associated first and second electrodes previously described, this embodiment may include a treatment device 250 disposed at the distal end 36 of the treatment catheter 20. Such a treatment device 250 may include exposed electrode portions 252 of one or more electrodes 256 disposed and positioned on at least a lower periphery of the treatment device 250 with markers 258 associated with each of the exposed electrode portions 252.

Referring now to FIGS. 12 and 12A, the treatment device 250 may be moved between a constricted position and an expanded position. In the constricted position, the treatment device 250 may be disposed within the treatment catheter 20 and, upon the treatment device 250 being moved relative to the distal end 36 of the treatment catheter 20, the treatment device may be deployed. Such movement of the treatment device 250 may be employed by either moving the treatment catheter 20 proximally relative to the treatment device 250 or the treatment device 250 may be moved distally to move the treatment device 250 relative to the distal end 36 of the treatment catheter 20. In this manner, the treatment device 250 may be deployed to radially self-expand to the expanded position.

In the expanded position, the treatment device 250 may exhibit a basket-like configuration formed of a weaved structure 260 with multiple strands 262. Such multiple strands 262 may include a super-elastic material, such as Nitinol wires, that may be insulated with a polymer formed thereon. The treatment device 250 may define an axis 264 extending co-axially or parallel with the treatment catheter 20 such that the treatment device 250 may be configured to radially expand from and relative to the axis 264. Such weaved structure 260 may include various configurations to radially expand and conform to a valve annulus. For example, the treatment device 250 may include a proximal side 266 and a distal side 268, the proximal side 266 radially extending with a generally convex periphery and the distal side including a lip 270 and pad portion 272 extending along a lower or distal periphery of the treatment device 250. The distal side 268 may also define a concave portion 274 extending along the periphery of the distal side 268. Further, the treatment device 250, in a fully expanded position, may include a substantially circular profile to exhibit an arcuate structure along the periphery (viewing the device from the proximal or distal sides). However, the weaved structure 260 of the treatment device 250 allows for the profile or lip 270 of the treatment device 250 to conform to the size of the annulus of the valve. In this manner, the profile of the treatment device 250 may conform to an oval or kidney-bean shape, or any other valve shape. For example, FIG. 14 depicts a simplified view of the treatment device 250 in the expanded position positioned over a mitral valve 170, depicting a profile of the treatment device 250 conforming to a tissue shelf 179 (see also FIG. 13) of the annulus 177 of the mitral valve 170 with the one or more electrodes 256 in contact with the valve annulus.

With respect to FIGS. 12 and 14, as set forth above, the lower periphery or pad portion 272 of the treatment device 250 may include multiple exposed electrode portions 252 of one or more electrodes 256. Such exposed electrode portions 252 may be spaced along the pad portion 272 of the treatment device 270 and adjacent an edge or lip 270 between the proximal side 266 and distal side 268 of the treatment device 250. Each of the exposed electrode portions 252 may include a conductive line 276 extending therefrom. Each of the conductive lines 276 may extend through the lumen of the treatment catheter 20 and to the RF energy source 16 (FIG. 1). With this arrangement, a physician may selectively activate particular ones of the exposed electrode portions 252 for treating selective portions of the annulus 177, described in further detail herein. The selected exposed electrode portions 252 may act as a single electrode or operate as multiple electrodes. Further, the treatment device 250 of this embodiment may operate in at least one of unipolar mode and bipolar mode, similar to that set forth and described relative to FIGS. 2A and 2B.

To assist the physician in selectively activating particular ones of the exposed electrode portions 252, each of the exposed electrode portions 252 may include a marker 258 associated therewith. In one embodiment, the exposed electrode portions 252 themselves may be formed of a conductive and a highly dense radiopaque material to act as the marker. In another embodiment, the markers 258 may be positioned and formed immediately adjacent each of the exposed electrode portions 252. Further, in another embodiment, one exposed electrode portion may include a reference marker (not shown) distinct from the other markers associated with the exposed electrode portions 252 in order to properly select particular ones of the exposed electrode portions. In another embodiment, a portion of the treatment device 250 may include a reference marker so that a physician can readily determine and select which exposed electrode portions to activate.

Further, as set forth in previous embodiments, the treatment device 250 may include one or more temperature sensors 280. The one or more temperature sensors 280 may be positioned along the pad portion 272 or adjacent to the lip 270 of the treatment device 250 and may be sized and configured to sense a temperature of the tissue being treated. Such one or more temperature sensors 280 may be coupled to the controller and RF energy source to assist a physician in treating the tissue of the valve within a temperature range, as previously set forth herein (see FIG. 1).

Figure 15:
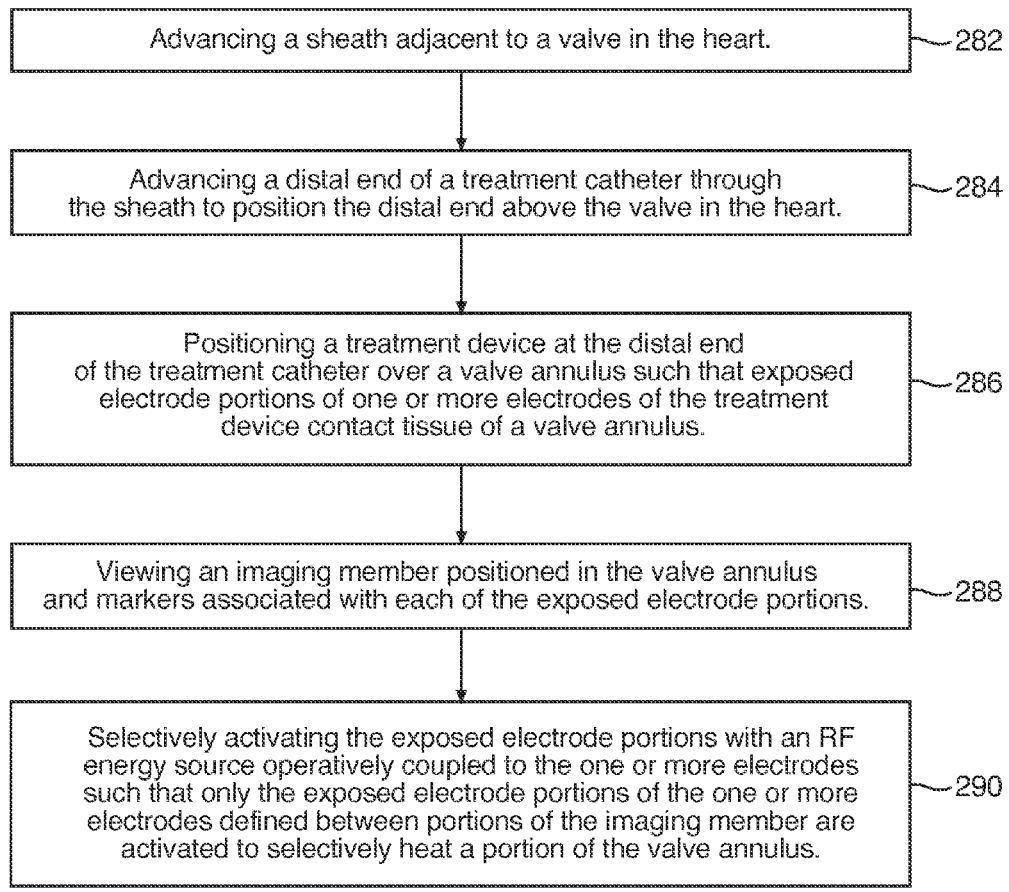
FIG. 15 is a block diagram of method steps for treating a valve in the heat, according to another embodiment of the present invention.

Now with primary reference to FIGS. 13, 14, and 15, a method for treating the annulus 177 of a valve, such as a mitral valve 170, with the treatment device 250 will be described. It should be noted that the treatment device 250 is not limited to being employed with the mitral valve 170, but may be implemented with other valves in, for example, the heart.

As set forth in step 282, a physician may advance the distal end 24 of the sheath 14 through the vascular system so that the distal end 36 of the sheath is positioned adjacent a valve in a heart (similar to that previously described in reference to FIGS. 4 and 5) so that the imaging member 80 may be advanced through the sheath 14 and positioned within the valve and provide orientation information to the physician relative to the valve. As set forth in step 284, the physician may then advance the distal end 36 of the treatment catheter 20 through the sheath 14 to center and position the distal end 36 of the treatment catheter 20 adjacent to and above the mitral valve 170. Upon positioning the distal end 36 of the treatment catheter 20, the treatment device 250 may be deployed from the treatment catheter 20. FIG. 13 depicts the treatment device 250 partially deployed from the treatment catheter 20 in a substantially centered position above the mitral valve 170. As the treatment device 250 is being deployed, the treatment device 250 radially expands and conforms to (or nests with) the tissue shelf 179 defining the annulus 177 of the mitral valve 170. In this manner, as set forth in step 286, the physician may position the treatment device 250 over the mitral valve 170 such that the exposed electrode portions 252 of the one or more electrodes 256 contact tissue of the valve annulus 177, as depicted in FIG. 14. The physician may then view the imaging member 80 and the markers 258 associated with each of the exposed electrode portions 252, as indicated in step 288. As in previous embodiments, typical imaging techniques may be employed as known to one of ordinary skill in the art. Such imaging techniques allow the physician to readily determine the posterior portion 180 (or posterior annulus) of the valve annulus 177 since the first and second shoulder portions 84, 86 of the imaging member 80 define and separate the posterior and anterior portions 180, 182 of the valve annulus 177. Further, the physician may then determine which exposed electrode portions 252 of the treatment device 250 are positioned over the posterior annulus 180 and are between the first and second shoulder portions 84, 86 of the imaging member 80 via the markers 258 associated with each of the exposed electrode portions 252. In this manner, as indicated in step 290, the physician may selectively activate the particular exposed electrode portions 252 positioned between the first and second shoulder portions 84, 86 of the imaging member 180 that are positioned over the posterior portion 180 of the valve annulus 177.

With respect to FIGS. 1 and 14, as in previous embodiments, the one or more electrodes 256 are operatively coupled to the RF energy source 16 and may be activated by the physician from the RF energy source to provide RF energy to the one or more electrodes 256 of the treatment device 250 to treat the desired tissue of the valve annulus 177. The RF energy source 16 may include input controls (not shown) to distinguish and activate the particular exposed electrode portions 252 selected by the physician. Further, as in previous embodiments, the treatment device 250 may include one or more temperature sensors 280 operatively coupled to the controller 18 and the RF energy source 16. As such, as the tissue is receiving RF energy, the one or more temperature sensors 280 may sense the tissue temperature and automatically control the RF energy source 16 once the desired temperature of the tissue has been reached so that the tissue is not over heated.

Figure 16:
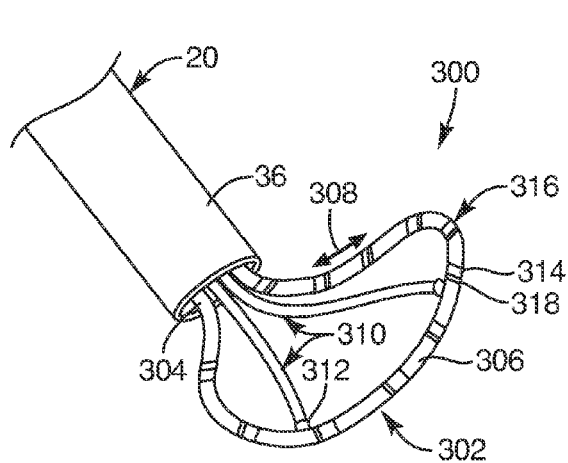
FIG. 16 is a perspective view of another embodiment of a medical device, depicting the medical device having an expandable and retractable loop configuration, according to the present invention.
Figure 16A:
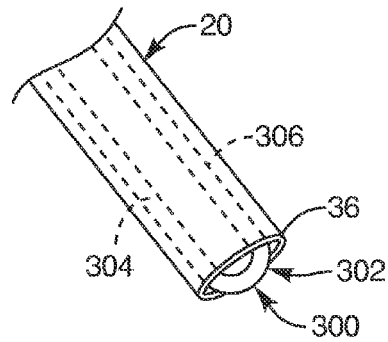
FIG. 16A is a perspective view of the medical device of FIG. 16, depicting the medical device in a constricted position within the treatment catheter, according to another embodiment of the present invention.

Now with reference to FIGS. 16 and 16A, another embodiment of a treatment device 300 is provided. In this embodiment, the treatment device 300 may be in the form of an expandable loop or expandable arcuate portion. The treatment device 300 may include an elongate structure 302 having a first elongate portion 304 and a second elongate portion 306. The elongate structure 302 may be conformable and flexible so as to facilitate the elongate structure 302 to be moved between a constricted position and an exposed or expanded position. In the constricted position, the first and second elongate portions 304, 306 may be positioned alongside each other within the treatment catheter 20 with a tight bend at the distal end 36 of the treatment catheter 20 where the first and second elongated portions 304, 306 extend from each other. In the exposed or expanded position, the elongate structure 302 may be deployed from the distal end 36 of the treatment catheter 20 to exhibit a loop configuration or an arcuate configuration or structure. The loop configuration may be substantially similar to a shape of the particular valve to be treated, such as a kidney-bean shape for the mitral valve, and may be pre-disposed to form such shape.

As set forth, the elongate structure 302 may include the first and second elongate portions 304, 306. In one embodiment, the first elongate portion 304 may be configured to maintain a fixed linear position relative to the distal end 36 of the treatment catheter 20. In other words, the first elongate portion 304 may be fixed so as to not move distally or proximally relative to the distal end 36 of the treatment catheter 20. The first elongate portion 304 may be at least partially positioned at a distal portion of the treatment catheter 20 and may only be slightly exposed at the distal end 36. With the first elongate portion 304 fixed, the second elongate portion 306 may be linearly moveable distally and proximally, as shown with bi-directional arrow 308, relative to the distal end 36 of the treatment catheter 20. Upon distal movement of the second elongate portion 306, the elongate structure 302 of the treatment device 300 may be deployed and may expand to the loop configuration. Further, the size of the loop configuration may be controlled by a length by which the second elongate portion 306 is moved distally. As such, the treatment device 300 of this embodiment may be sized in real-time to nest appropriately with the size of a particular valve, such as the mitral valve. Further, the second elongate portion 306 may be sized and configured to self-expand to, for example, a kidney-bean shape or to the shape of the valve annulus that the treatment device 300 is intended to treat. With this arrangement, the treatment device 300 may be positioned within various sized valves. In another embodiment, the first and second elongate portions 304, 306 of the treatment device 300 may both move proximally and distally relative to the distal end 36 of the treatment catheter 20.

In another embodiment, the elongate structure 302 of the treatment device 300 may also include one or more stabilizing members 310. Such one or more stabilizing members 310 may be sized and configured to facilitate pulling and pushing of the elongate structure 302. Each of the one or more stabilizing members 310 may be coupled to a separate location of the elongate structure 302 and extend through the treatment catheter 20 to the handle (not shown) so as to facilitate control of pulling or pushing the elongate structure 302 to stabilize the treatment device 300 at the valve. In this manner, the physician may be able to operate actuators or controls at the handle (not shown) to apply pressure to the elongate structure or to assist the physician in obtaining optimal position of the elongate structure 302 over the valve annulus.

Each of the one or more stabilizing members 310 may include a line and a coil combination to facilitate pulling and pushing on the elongate structure 302. The line may be coupled to a coupler 312, such as a latch or the like, positioned on the elongate structure 302 and extend through the coil. The line may be a wire made of stainless steel, Nitinol, a polymer or any other suitable wire structure. The coil may be formed with one or more wires and may be woven and/or a helical structure. The coil may include a polymer wrap that may be attached with heat, for example. With this arrangement, the line may facilitate pulling the elongate structure 302 to assist in positioning the elongate structure 302 over the valve annulus and the coil may facilitate the pushing of the elongate structure 302 to assist in positioning and stabilizing the elongate structure over the valve annulus.

In addition, the treatment device 300 may include exposed electrode portions 314 of one or more electrodes 316. The exposed electrode portions 314 may be spaced along the elongate structure 302 of the treatment device 300. In one embodiment, the exposed electrode portions 314 may be positioned along the second elongate portion 306 of the elongate structure 302. As in the previous embodiment, the exposed electrode portions 314 may operate as a single electrode or as multiple electrodes. Further, each of the exposed electrode portions 314 may include a marker 318 associated therewith. With this arrangement, a physician may select particular electrode portions of the exposed electrode portions 314 to be activated. Furthermore, the treatment device 300 may include one or more temperature sensors (not shown) for sensing a temperature of the tissue being treated. Such one or more temperature sensors may be operatively coupled to the controller 18 and RF energy source 16 (FIG. 1) to control and as a safe guard against the RF energy overheating the valve annulus, as previously set forth herein. In one embodiment, the one or more temperature sensors may be positioned adjacent to and between some or each of the exposed electrode portions 314. In another embodiment, the one or more temperature sensors may extend through, for example, the coil portion of the one or more stabilizing members 310 such that the temperature sensor may be linearly moveable distally to the tissue to sense the temperature thereof.

Figure 17:
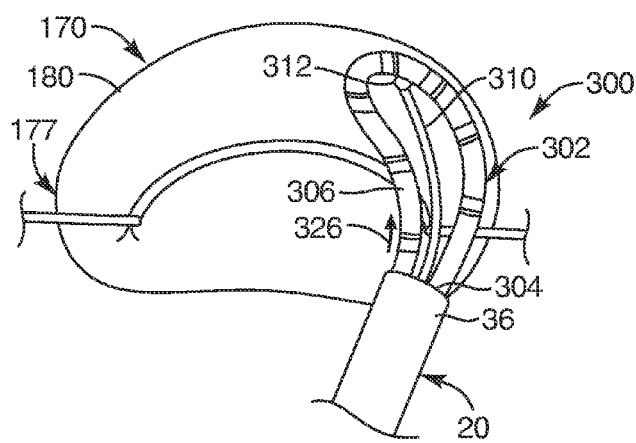
FIG. 17 is a perspective view of the medical device of FIG. 16, depicting the medical device partially deployed over a posterior annulus of a valve, according to another embodiment of the present invention.
Figure 18:
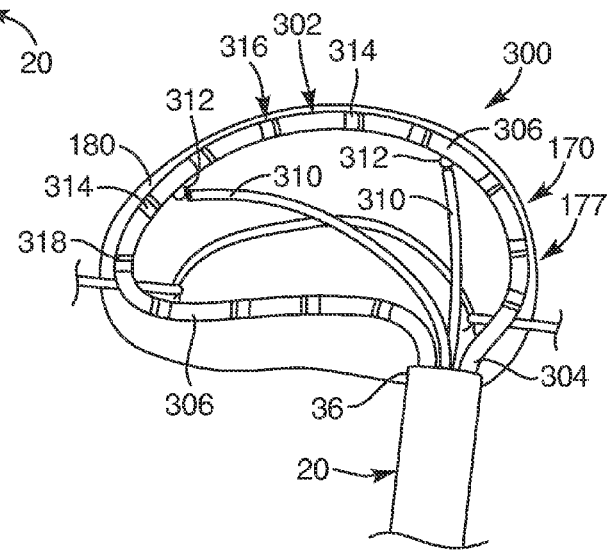
FIG. 18 is a perspective view of the medical device of FIG. 16, depicting the medical device fully deployed over the posterior annulus of the valve, according to another embodiment of the present invention.

Now with reference to FIGS. 17 and 18, description of positioning and treating the valve annulus 177 with the expandable loop treatment device 300 will now be provided. Prior to positioning the treatment device 300 of this embodiment, the imaging member 80 may be positioned in the valve with the first and second shoulder portions 84, 86 of the imaging member 80 positioned over the valve annulus 177 to define the posterior and anterior portions 180, 182 of the annulus, as set forth in previous embodiments. The physician may then position the distal end 36 of the treatment catheter 20 adjacent one of the shoulder portions, for example, the second shoulder portion 86 in preparation for positioning the treatment device 300 over a portion of the annulus, for example, the posterior portion 180 of the valve annulus 177. As in previous embodiments, the imaging member 80 includes various markers so that the physician can readily determine the location for positioning the distal end 36 of the treatment catheter 20.

Once the distal end 36 of the treatment catheter 20 is positioned adjacent the second shoulder portion 86 of the imaging member 80, the physician may distally move (as shown by directional arrow 326) the second elongate portion 306 of the treatment device 300 to begin forming and expanding the loop configuration, as depicted in FIG. 17. By maintaining the distal end 36 of the treatment catheter 20 adjacent the second shoulder portion 86 of the imaging member 80 and applying pressure or slightly pushing on the one or more stabilizing members 310, the loop configuration of the treatment device 300 may be stabilized in the valve annulus 177. If it is determined that a portion of the second elongate portion 306 is not appropriately positioned, the physician may manipulate the second elongate portion 306 by pulling the stabilizing member 310 and then pushing the stabilizing member 310 into the appropriate position over the posterior portion 180 of the valve annulus 177. If the treatment device 300 is completely moved from the annulus 177, the physician may withdraw the second elongate portion 306 proximally into the treatment catheter 20 and then deploy the treatment device 300 again employing the method set forth above to obtain a desired position over the annulus 177.

As depicted in FIG. 18, upon positioning the loop configuration of the treatment device 300 over the valve annulus 177, the physician may readily view the markers 318 associated with each of the exposed electrode portions 314 as well as the first and second shoulder portions 84, 86 of the imaging member 80 by employing known imaging techniques. As in the previous embodiment, the physician may then selectively activate the exposed electrode portions 314 positioned between the first and second shoulder portions 84, 86 of the imaging member 80 to selectively treat the posterior portion 180 of the valve annulus 177. In this manner, each of the method steps provided for in FIG. 15 and described relative thereto are applicable in this embodiment for treating the valve annulus 177, as will be readily understood by one of ordinary skill in the art.

Figure 19:
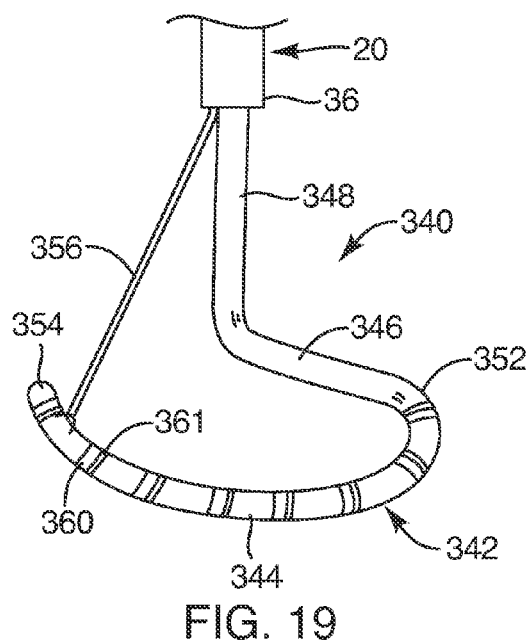
FIGS. 19 and 20 are perspective views of another embodiment of a medical device, depicting the medical device having an arcuate configuration with a pusher/puller portion, according to the present invention.
Figure 20:
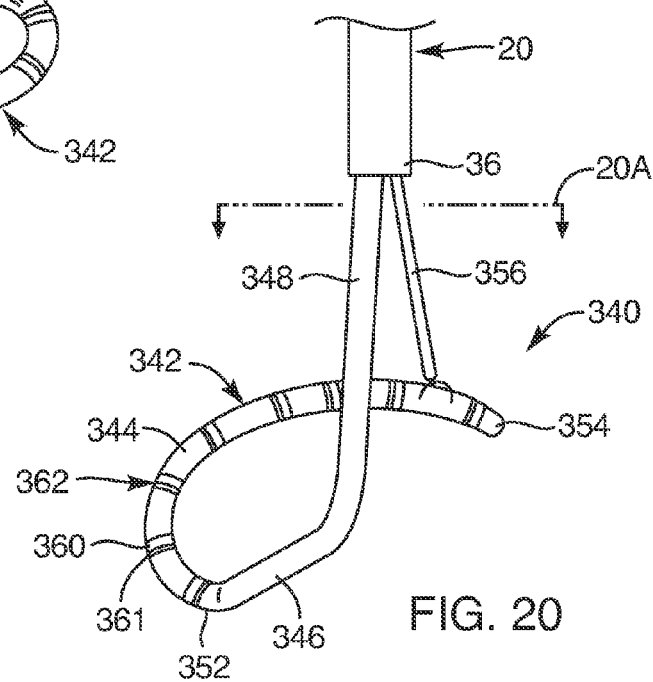
Figure 20A:
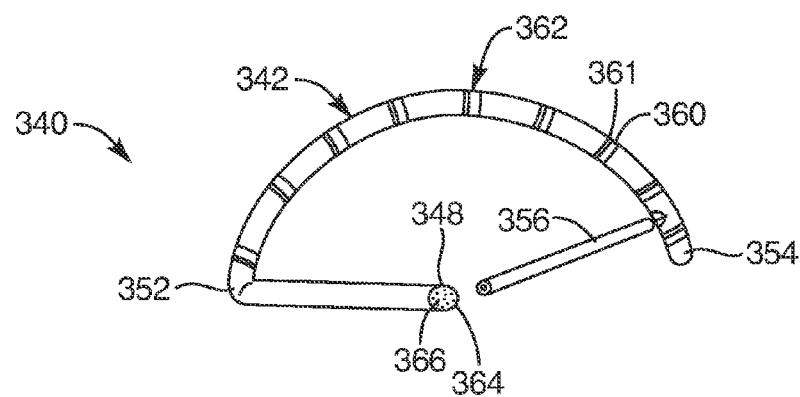
FIG. 20A is a cross-section view of the medical device taken along section line 20A of FIG. 20, depicting the arcuate configuration of the medical device, according to the present invention.

FIGS. 19, 20, and 20A depict another embodiment of a treatment device 340 disposed at the distal end 36 of the treatment catheter 20 of the present invention. In this embodiment, the treatment device 340 may include an elongate structure 342 that may move between constricted and expanded positions, the constricted position being disposed within the treatment catheter 20 and/or sheath 14 (FIG. 1) and the expanded position being deployed from the treatment catheter 20 or sheath 14. The elongate structure 342 may include a treatment portion 344, an arm portion 346 and a body portion 348. The treatment portion 344 may self-expand to an arcuate configuration or structure and may be configured to self-expand or extend to, for example, a shape similar to a posterior portion of a valve annulus. The treatment portion 344 may include a proximal end 352 and a distal free end 354, the proximal end 352 extending from the arm portion 346. The arm portion 346 may extend at an upward angle toward the body portion 348 of the treatment device 340. The body portion 348 may extend from the arm portion 346 and upward through the lumen of the distal end 36 of the treatment catheter 20. Similar to the previous embodiment, the treatment device 340 may include one or more stabilizing members 356, similar to the previous embodiment. At least one of the stabilizing members 356 may be coupled adjacent the distal free end 354 of the treatment device 340 so as to control and stabilize the treatment portion 344 of the treatment device 340 positioned over the valve annulus.

As in the previous embodiments, the treatment portion 344 may include exposed electrode portions 360 of one or more electrodes 362 that may be spaced along the arcuate configuration of the treatment portion 344. Further, the treatment device 340 may include one or more temperature sensors (not shown) operatively coupled to the controller 18 and RF energy source 16 (FIG. 1) so as to control the heating of the tissue of the valve annulus. Such one or more temperature sensors may be positioned between the exposed electrode portions 360 or may extend through the one or more stabilizing members 356. Furthermore, one or more of the exposed electrode portions 360 may include a marker 361 for imaging purposes and selection of particular electrode portions 360 to activate. As depicted in the cross-sectional view of the body portion 348 of FIG. 20A, the body portion 348 may define a lumen 364 through which multiple electrode lines 366 may extend. Each of such electrode lines 366 may correspond with one of the exposed electrode portions 360. Similar electrode lines 366 corresponding with the exposed electrode portions 360 may be employed with the elongate structure 302 depicted in the previous embodiment (see FIG. 16), as will be readily understood by one of ordinary skill in the art.

Figure 21:
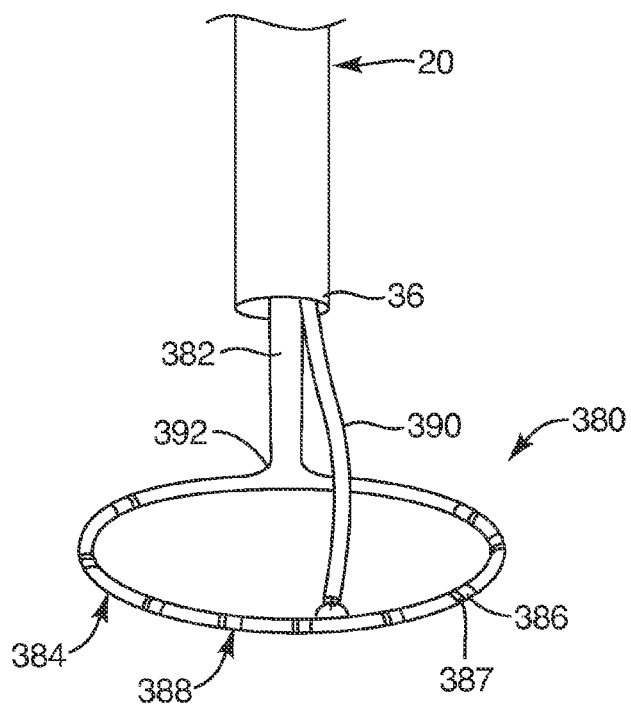
FIG. 21 is a front view of another embodiment of a medical device, depicting the medical device having a ring configuration in a first orientation, according to the present invention.
Figure 22:
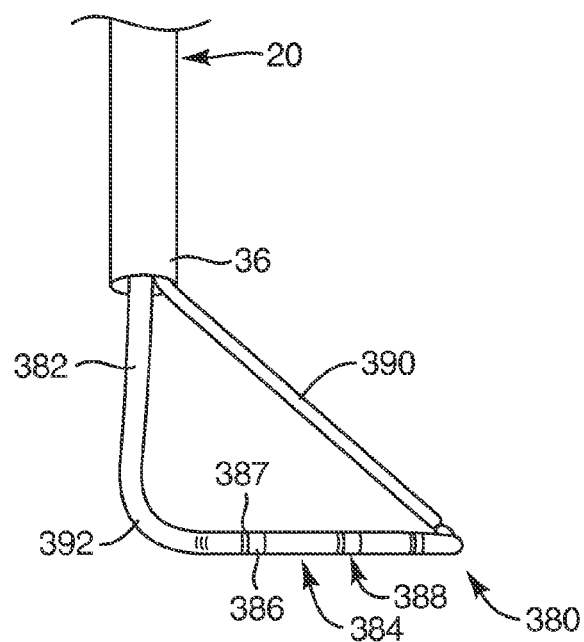
FIG. 22 is a side view of the medical device, depicting the medical device moved to a second orientation, according to another embodiment of the present invention.

Now with reference to FIGS. 21 and 22, another embodiment of a treatment device 380 disposed at the distal end 36 of the treatment catheter 20 is provided. The treatment device 380 of this embodiment may include a body portion 382 extending to a ring structure 384 or arcuate structure. The ring structure 384 may include exposed electrode portions 386 of one or more electrodes 388, as in the previous embodiments. Further, one or more of the exposed electrode portions 386 may be associated with a marker 387. The ring structure 384 may be circular shaped, oval shaped, or kidney-bean shaped, or any other suitable ring structure. The treatment device 380 may include a stabilizing member 390, similar to the previous embodiments. The body portion 382 may be bendable at a distal end 392 thereof such that, upon deploying the treatment device 380, the stabilizing member 390 may be pulled to bend the ring structure 384 to an orientation that corresponds with the valve annulus, as depicted in FIG. 22. With this arrangement, upon positioning the ring structure 384 over the annulus, the physician may view the markers 387 associated with the exposed electrode portions 386 relative to the first and second shoulder portions of the imaging member (not shown) and select particular ones of the exposed electrode portions 386 to activate and treat a portion of the annulus, such as the posterior annulus, similar to that described and set forth in previous embodiments. Further, as in previous embodiments, in conjunction with the controller 18, the treatment device 380 of this embodiment also may include one or more temperature sensors (not shown) operatively coupled to the controller 18 and RF energy source 16 to sense the temperature of the tissue being treated to ensure such tissue is not overly heated (see FIG. 1).

In another embodiment, the imaging member 80 set forth herein may be incorporated with the various embodiments of the treatment device. For example, the treatment device set forth in FIG. 12 may include an imaging member incorporated therewith that may extend distally of the treatment device with, for example, a U-shaped configuration, and self-orient within the valve. Another embodiment may include two elongated imaging members with atraumtic tips, such as J-shaped tips, one at each opposing side of the treatment device that may extend through the valve structure and self-orient therein so that the physician can readily determine a portion of the valve, such as the posterior annulus, to treat.

In another embodiment, the treatment device having an arcuate structure, similar to that shown in FIGS. 12, 16, 19, and 21, may include multiple imaging members coupled to and freely or loosely hanging from a distal side of the treatment device. For example, the treatment device may include four to ten imaging members (or more) that freely hang distally from the treatment device. Upon deploying the treatment device adjacently above the valve, the imaging members that maintain a distally extending position, such as two imaging members with one imaging member extending through the valve at each corner or end of the valve, may provide the orientation information of the valve for the physician. The other imaging members that do not extend through the valve will be readily apparent as the other imaging members may be moving due to the valve opening and closing or positioned laterally relative to the treatment device and along the periphery of the valve, such as adjacent to the posterior and anterior portions of the valve annulus. In this manner, the treatment device may include multiple imaging members such that some of the multiple imaging members may provide imaging information as to the orientation of the valve so that a physician can appropriately treat an intended portion of the valve, such as the posterior portion of a valve annulus.

While the invention may be susceptible to various modifications and alternative forms, specific embodiments have been shown by way of example in the drawings and have been described in detail herein. However, it should be understood that the invention is not intended to be limited to the particular forms disclosed. Rather, each embodiment disclosed herein may incorporate portions of the various embodiments disclosed herein. As such, the invention includes all modifications, equivalents, and alternatives falling within the spirit and scope of the invention as defined by the following appended claims.

What is claimed is:

1. A medical device system for treating a valve in a heart to minimize valve regurgitation, the medical device system comprising:
   a radio frequency energy source;
   a handle operatively coupled to the radio frequency energy source;
   a treatment catheter coupled to the handle, the treatment catheter extending between a proximal end and a distal end and including a lumen defined along a length of the treatment catheter;
   a treatment device disposed at the distal end of the treatment catheter, the treatment device moveable between a constricted position and an expanded position, the treatment device including multiple strands extending in a woven configuration and, in the expanded position, configured to be conformable to a valve annulus of the valve, the treatment device including a lower periphery with one or more exposed electrode portions of one or more electrodes, the one or more exposed electrode portions including markers associated therewith and the one or more exposed electrode portions configured to be selectively activated to heat a selective portion of the valve annulus; and
   an imaging member sized and configured to be positioned within the valve and configured to provide imaging information regarding orientation of the valve, the imaging member including a first shoulder portion and a second shoulder portion configured to be positioned against the valve annulus in a spaced manner so as to viewably orient and define the selective portion of the valve annulus to heat, wherein only the one or more exposed electrode portions of the treatment device positioned between the first and second shoulder portions of the imaging member are selectively activated to heat the selective portion of the valve annulus.

2. The medical device system of claim 1, further comprising a sheath defining a sheath lumen along a length of the sheath, the sheath lumen configured to provide a pathway to position the distal end of the treatment catheter adjacent the valve.

3. The medical device system of claim 1, wherein the lower periphery of the treatment device is conformable to nest with at least a portion of the valve annulus.

4. The medical device system of claim 1, wherein a distal side of the treatment device comprises a pad portion on which the one or more exposed electrode portions are positioned.

5. The medical device system of claim 1, wherein the treatment catheter is configured to be steerable along a distal portion of the treatment catheter such that the distal portion is moveable to multiple orientations.

6. The medical device system of claim 1, wherein the treatment device comprises one or more temperature sensors.

7. The medical device system of claim 6, further comprising a controller coupled to the radio frequency energy source and the one or more temperature sensors.

* * * * *